US009951344B2

(12) United States Patent
Alper et al.

(10) Patent No.: US 9,951,344 B2
(45) Date of Patent: Apr. 24, 2018

(54) EXOGENOUS TERMINATORS FOR CONTROLLING FUNGAL GENE EXPRESSION

(71) Applicant: Board of Regents, The University of Texas System, Austin, TX (US)

(72) Inventors: Hal Alper, Austin, TX (US); Kathleen Curran, Emeryville, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 53 days.

(21) Appl. No.: 14/879,946

(22) Filed: Oct. 9, 2015

(65) Prior Publication Data

US 2016/0102314 A1 Apr. 14, 2016

Related U.S. Application Data

(60) Provisional application No. 62/062,766, filed on Oct. 10, 2014.

(51) Int. Cl.
*C12N 1/15* (2006.01)
*C12N 15/80* (2006.01)

(52) U.S. Cl.
CPC .................... *C12N 15/80* (2013.01)

(58) Field of Classification Search
None
See application file for complete search history.

(56) References Cited

U.S. PATENT DOCUMENTS

| 7,851,612 B2 * | 12/2010 | Wilkinson | ......... C12N 15/8216 435/320.1 |
|---|---|---|---|
| 2005/0227246 A1 | 10/2005 | Hahm et al. | |
| 2007/0009932 A1 | 1/2007 | Stephanopoulos et al. | |
| 2013/0324440 A1 | 5/2013 | Roberts et al. | |

FOREIGN PATENT DOCUMENTS

| WO | 2001042447 A2 | 6/2001 |
|---|---|---|
| WO | 2012129036 A2 | 9/2012 |

OTHER PUBLICATIONS

International Search Report and Written Opinion issued in corresponding application No. PCT/US2015/058631, dated May 3, 2016, 17 pgs.
Liang, Jing et al., "Coordinated Induction of Multi-Gene Pathways in *Saccharomyces cerevisiae*," Nucleic Acids Research, 2013, vol. 41, No. 4, e54, pp. 1-10.
Khalil, Ahmad S. et al., "A Synthetic Biology Framework for Programming Eukaryotic Transcription Functions," Cell. Aug. 3, 2012, 150(3), pp. 647-658.
Vishwanath, Iyer et al., "Poly (dA:dT), A Ubiquitous Promoter Element That Stimulates Transcription Via Its Intrinsic DNA Structure," The EMBO Journal, vol. 14, No. 11, pp. 2570-2579, 1995.
Hanh, Steven et al., "Transcriptional Regulation in *Saccharomyces cervisiae*: Transcription Factor Regulation and Function, Mechanisms of Initiation, and Roles of Activators and Coactivators," Genetics, vol. 189, pp. 705-736, Nov. 2011.
Du, Jing et al., "Customized Optimization of Metabolic Pathways by Combinatorial Transcriptional Engineering," Nucleic Acids Research, vol. 40, No. 18, e142, 2012, pp. 1-10.
Curran, Kathleen A. et al., "Design of Synthetic Yeast Promoters via Tuning of Nucleosome Architecture," Nat commun.; 5: 4002. doi: 10.1038/ncomms5002, Nov. 27, 2014, pp. 1-20.
Curran, Kathleen A. et al., "Use of High Capacity Terminators in *Saccharomyces cerevisiae* to Increase mRNA Half-Life and Improve Gene Expression Control for Metabolic Engineering Applications," Metab Eng. Sep. 2013; 19: 88-97. doi:10.1016/j.ymben.2013.07.001, Sep. 1, 2014, pp. 1-24.
Chen, Wei et al., "Yeast mRNA Initiation Sites Are Determined Primarily by Specific Sequences, Not by the Distance from the TATA Element," The EMBO Journal, vol. 4, No. 12, pp. 3273-3280, 1985.
Blount, Benjamin A et al, "Rational Diversification of a Promoter Providing Fine-Tuned Expression and Orthogonal Regulation for Synthetic Biology," PLoS ONE, vol. 7, issue 3, e33279, Mar. 2012, pp. 1-11.
Bhaumik, Sukesh R. et al., "Differential Requirement of SAGA Components for Recruitment of TATA-Box-Binding Protein to Promoters In Vivo," Molecular and Cellular Bioloby, vol. 22, No. 21, pp. 7365-7371, Nov. 2002.
Zhang, Zhihong et al., "Mapping of Transcription Start Sites in *Saccharomyces cerevisiae* Using 5' SAGE," Nucleic Acids Research, vol. 33, No. 9, doi:10.1093/nar/gki583, pp. 2838-2851, 2005.
Teng, Xinchen et al., "Genome-Wide Consequences of Deleting Any Single Gene," Molecular and Cellular Biology, vol. 52, No. 4, doi:10.1016/j.molce1.2013.09.026, pp. 485-494, Nov. 21, 2013.
Teixeira, Miguel Cacho et al., "The YEASTRACT Database: An Upgrade Information System for the Analysis of Gene and Genomic Transcription Regulation in *Saccharomyces cerevisiae*," Nucleic Acids Research, vol. 42, doi:10.1093/nar/gkt1015, pp. D161-D166, 2014.
Sharon, Eilon et al., "Inferring Gene Regulatory Logic from High-Throughput Measurements of Thousands of Systematically Designed Promoters," Nat Biotechnol.; 30(6); doi:10.1038/nbt.2205; pp. 521-530, 2012.
Rhee, Ho Sung et al., "Genome-Wide Structure and Organization of Eukaryotic Preinitiation Complexes," Nature; 483(7389): 295-301; doi:10.1038/nature10799; pp. 1-14, 2012.
Nevoigt, Elke et al., "Engineering of Promoter Replacement Cassettes for Fine-Tuning of Gene Expression in *Saccharomyces cerevisiae*," Applied and Environmental Microbiology, vol. 72, No. 8., pp. 5266-5273, Aug. 2006.
Mohibullah, Neeman et al., "Site-Specific Cross-Linking of TBP in Vivo and in Vitro Reveals a Direct Functional Interaction with the SAGA Submit Spt3," Genes & Development 22, pp. 2994-3006; 2008.

(Continued)

*Primary Examiner* — James S Ketter
(74) *Attorney, Agent, or Firm* — Meunier Carlin & Curfman LLC

(57) ABSTRACT

Provided herein are exogenous terminator sequences for use in fungi cell transcriptional termination.

18 Claims, 6 Drawing Sheets

(56) References Cited

OTHER PUBLICATIONS

Lubliner, Shai et al., "Sequence Features of Yeast and Human Core Promoters That Are Predictive of Maximal Promoter Activity," Nucleic Acids Research, vol. 41, No. 11, doi:10.1093/nar/gkt256; pp. 5569-5581; 2013.

Ligr, Martin et al., "Gene Expression From Random Libraries of Yeast Promoters," Genetics Society of America, vol. 172, pp. 2113-2122, Apr. 2006.

* cited by examiner

EXOGENOUS TERMINATORS FOR CONTROLLING FUNGAL GENE EXPRESSION

CROSS-REFERENCES TO RELATED APPLICATIONS

This application claims the benefit of U.S. Provisional Application No. 62/062,766, filed Oct. 10, 2014, the content of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under Grant No. GM090221 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48932-527001US_ST25.TXT, created Oct. 8, 2015, 13,467 bytes, machine format IBM-PC, MS-Windows operating system, is hereby incorporated by reference.

BACKGROUND OF THE INVENTION

Commonly used expression constructs and synthetic biology tools in fungi cells use native terminator sequences to end transcription. These native terminator sequences are lengthy, typically greater than 500-1000 base pairs in length. This length imposes additional transcription burden on the cell as well as foreclosing synthesis in a lab on large scale. Thus, there is a need in the art for short exogenous terminator sequences in fungi cells. Provided here are solutions to these and other problems in the art.

BRIEF SUMMARY OF THE INVENTION

Provided herein, inter alia, are short exogenous fungi cell terminators and methods for using the exogenous terminators for fungi cell transcription. The terminators may increase net RNA output and lessen the burden on cells during transcription.

In a first aspect is an exogenous fungi transcription terminating nucleic acid sequence that includes an efficiency nucleic acid sequence of the formula $(TA)_{n1}$, where n1 is an integer from 4 to 20 and a positioning nucleic acid sequence of the formula AAWAAA, where W is A or T. The exogenous fungi transcription terminating nucleic acid sequence further includes a polyadenylation site nucleic acid sequence having the sequence $(N)_{n4}Y-A_{n2}$, where the symbol N is A, C, T, or G and the symbol n4 is an integer from 0 to 10. Y is a polyadenylation site nucleotide and is C or T. The symbol n2 is an integer from 3 to 50.

In another aspect is an exogenous fungi transcription terminating nucleic acid sequence that includes an efficiency nucleic acid sequence of the formula $(TA)_{n1}$, where n1 is an integer from 3 to 20 and a positioning nucleic acid sequence of the formula AAWAAA, where W is A or T. The exogenous fungi transcription terminating nucleic acid sequence further includes a polyadenylation site nucleic acid sequence having the sequence $(N)_{n4}Y-A_{n2}$, where the symbol N is A, C, T, or G and the symbol n4 is an integer from 0 to 10. Y is a polyadenylation site nucleotide and is C or T. The symbol n2 is an integer from 3 to 50. The exogenous fungi transcription terminating nucleic acid sequence further includes a first linking nucleic acid sequence linking the positioning nucleic acid sequence to the efficiency nucleic acid sequence or a second linking nucleic acid sequence linking the positioning nucleic acid sequence to the polyadenylation site nucleic acid sequence, where the first linking nucleic acid and the second linking nucleic acid are independently 3 to 30 nucleotides in length and consist of less than about 35% of cytosine and guanine.

In another aspect is an exogenous fungi transcription terminating nucleic acid sequence that includes an efficiency nucleic acid sequence of the formula $(TA)_{n1}$, where n1 is an integer from 3 to 20 and a positioning nucleic acid sequence of the formula AAWAAA, where W is A or T. The exogenous fungi transcription terminating nucleic acid sequence further includes a polyadenylation site nucleic acid sequence having the sequence $(N)_{n4}Y-A_{n2}$, where the symbol N is A, C, T, or G and the symbol n4 is an integer from 0 to 10. Y is a polyadenylation site nucleotide and is C or T. The symbol n2 is an integer from 3 to 50. The exogenous fungi transcription terminating nucleic acid sequence further includes an upstream nucleic acid sequence 5' to the efficiency nucleic acid sequence of the formula $(T)_{n3}$, where n3 is an integer from 2 to 20.

Further provided herein is a fungi cell that includes an exogenous fungi transcription terminating nucleic acid sequence described herein.

Provided herein are expression constructs. In one aspect is an expression construct that includes an exogenous fungi transcription terminating nucleic acid sequence described herein.

Further provided herein are methods of expressing a gene in a fungi cell. In one aspect is a method of expressing a gene in a fungi cell by transforming a fungi cell with an expression construct that includes a gene operably linked to an exogenous fungi transcription terminating nucleic acid sequence described herein. The method further includes allowing the cell to express the expression construct, where the exogenous fungi transcription terminating nucleic acid sequence modulates a level of transcription of the gene, thereby expressing the gene in the fungi cell.

Tsynth14=SEQ ID NO:14. Tsynth15=SEQ ID NO:15.
Tsynth16=SEQ ID NO:16. Tsynth17=SEQ ID NO:17.
Tsynth18=SEQ ID NO:18. Tsynth19=SEQ ID NO:19.
Tsynth20=SEQ ID NO:20. Tsynth21=SEQ ID NO:21.
Tsynth22=SEQ ID NO:22. Tsynth23=SEQ ID NO:23.
Tsynth24=SEQ ID NO:24. Tsynth25=SEQ ID NO:25.
Tsynth26=SEQ ID NO:26. Tsynth27=SEQ ID NO:27.
Tsynth28=SEQ ID NO:28. Tsynth29=SEQ ID NO:29.
Tsynth30=SEQ ID NO:30.

Figure 3:
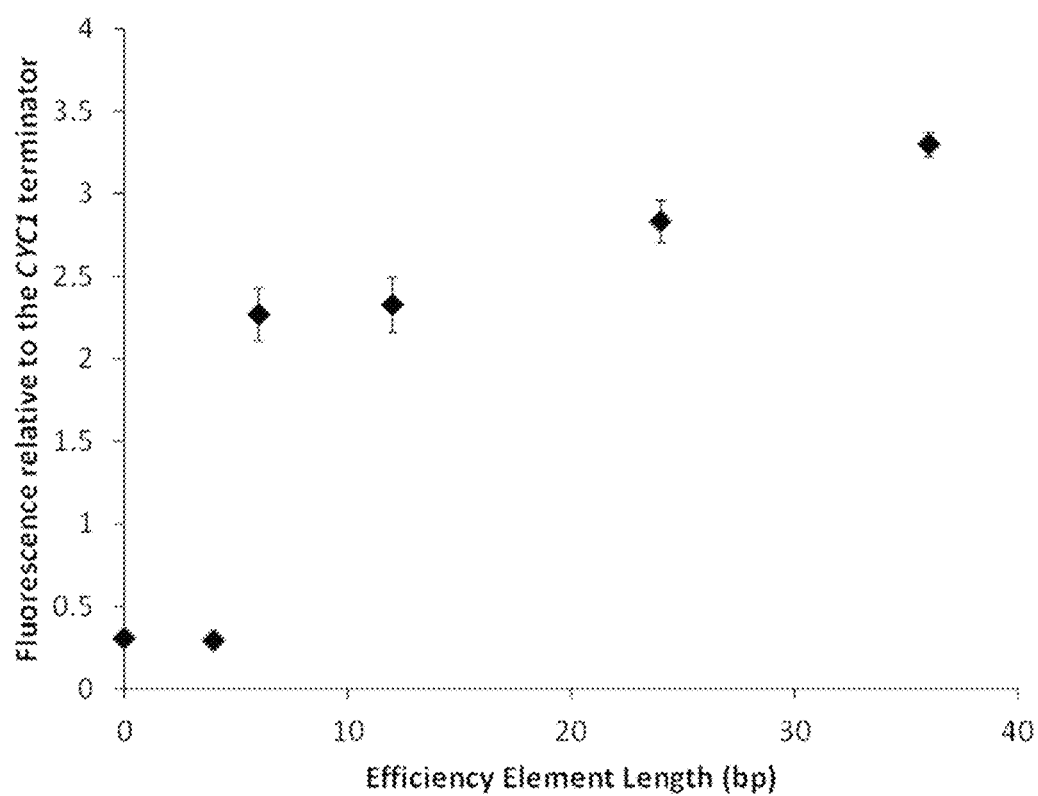

FIG. 3 depicts effect of efficiency element length (BP) (x-axis) on fluorescence relative to the CYC1 terminator. Efficiency element length correlates with relative protein expression, and there is a clear requirement for elements to be at least 6 bp long.

Figure 4:
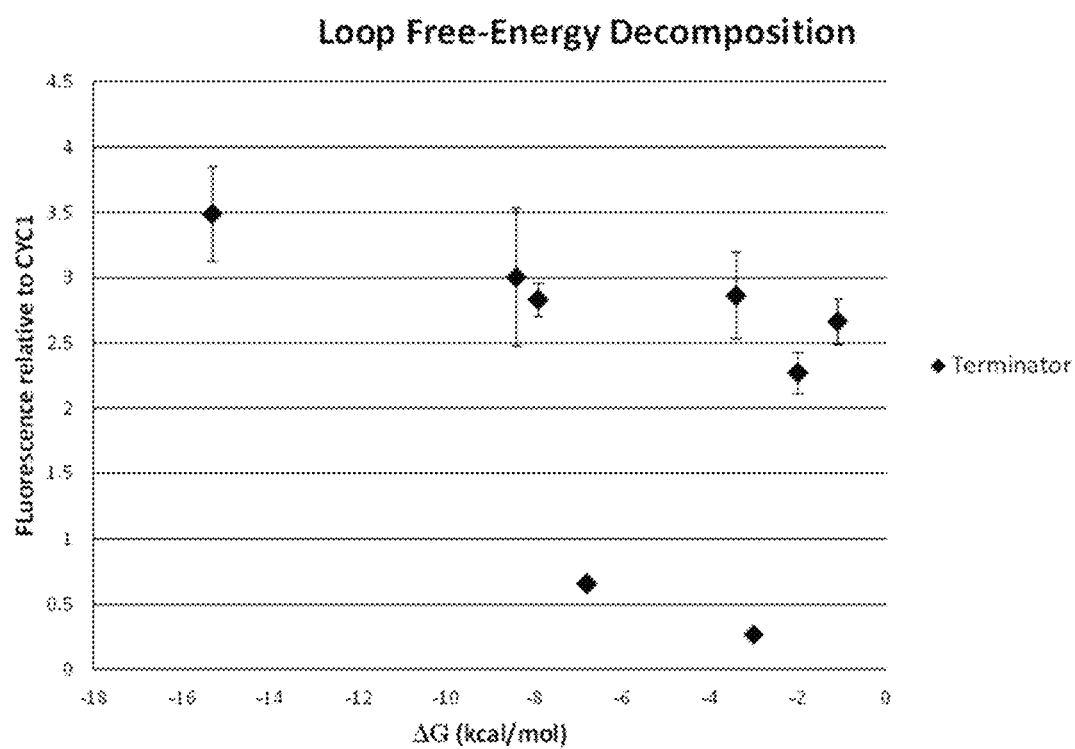

FIG. 4 depicts results of loop free-energy decomposition, X-axis: DG (kcal/mol); Y-axis: fluorescence relative to CYC1. The calculations were conducted using the mfold program (The RNA Institute, University of Albany, Albany N.Y.).

Figure 5:
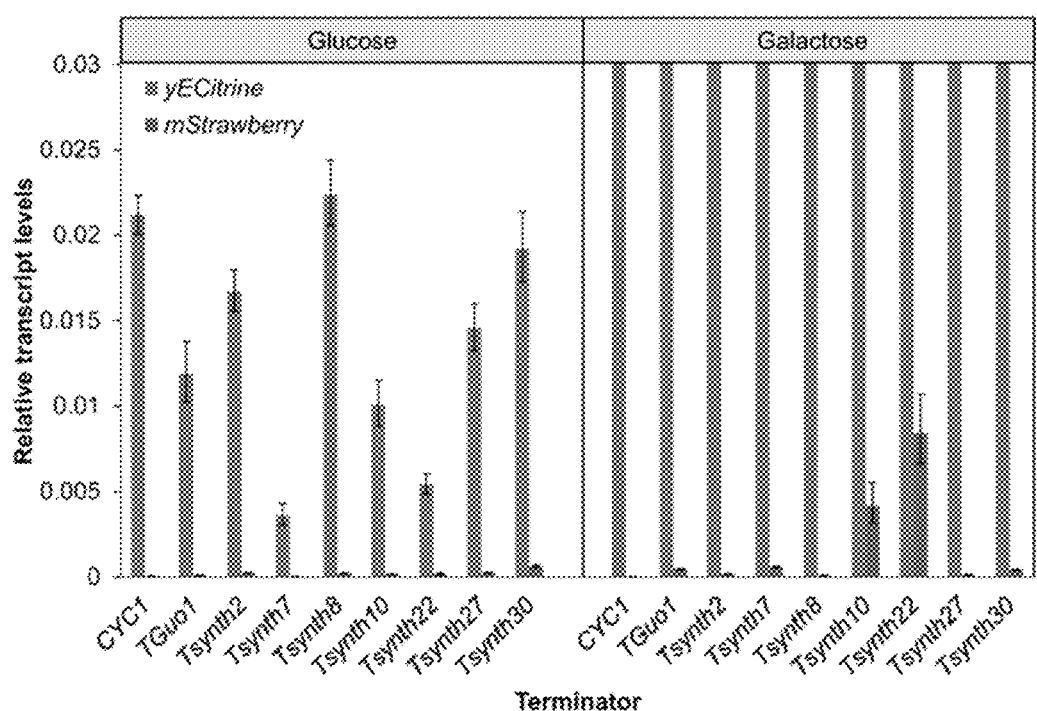

FIG. 5 depict the termination efficiency of selected native and synthetic terminators. Transcript levels of yECitrine and mStrawberry placed on either side of the terminator of interest were measured. In glucose media, the GAL1 promoter is repressed and higher mStrawberry transcript levels likely indicates cryptic promoter activity in the terminator. In galactose media, the GAL1 promoter is induced and higher mStrawberry transcript levels indicates insufficient transcription termination and read-through. In FIG. 5 the y-axis is adjusted to show the smallest values. Error bars are propagated standard deviations from three technical replicates of each qPCR. Legend (left to right): CYC1, (TGuo1=SEQ ID NO:31), (Tsynth2=SEQ ID NO:2), (Tsynth7=SEQ ID NO: 7), (Tsynth8=SEQ ID NO:8), (Tsynth10=SEQ ID NO:10), (Tsynth22=SEQ ID NO:22), (Tsynth27=SEQ ID NO:27) and (Tsynth30=SEQ ID NO: 30).

Figure 6A:
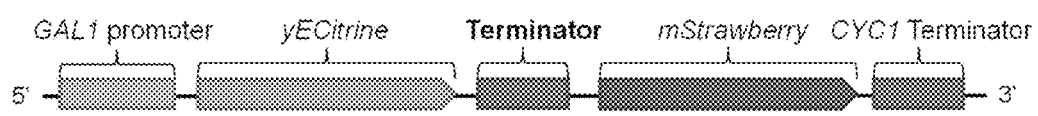
Figure 6B:
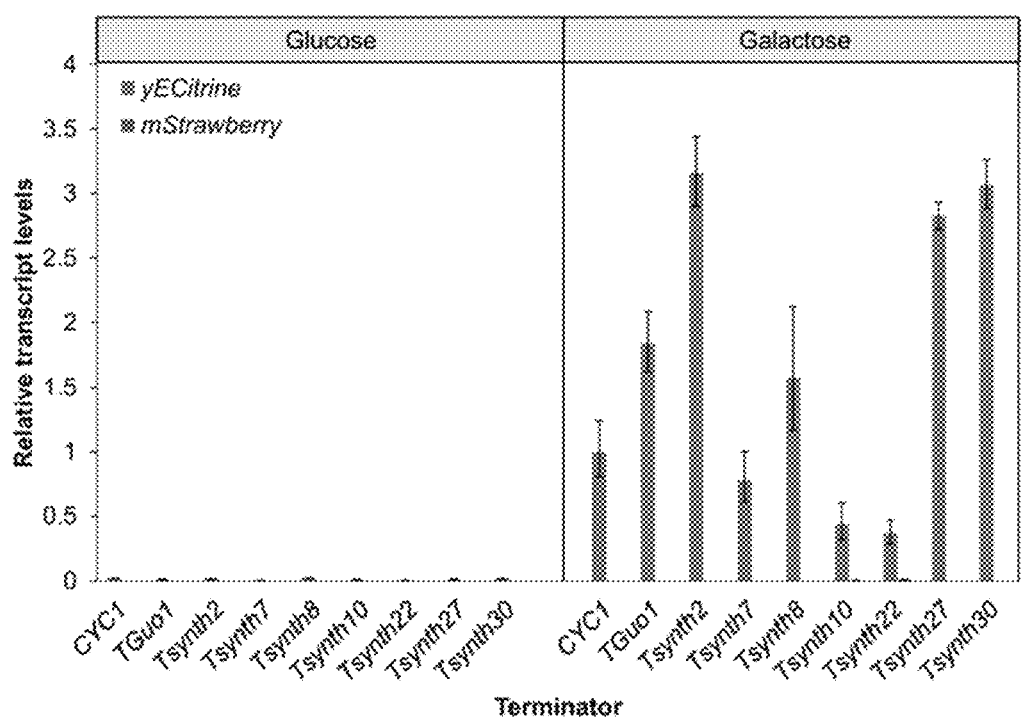

FIGS. 6A-6B depict the termination efficiency of selected native and synthetic terminators. FIG. 6A depicts a diagram of construct to test termination efficiency. Transcript levels of yECitrine and mStrawberry placed on either side of the terminator of interest were measured. In glucose media, the GAL1 promoter is repressed and higher mStrawberry transcript levels likely indicates cryptic promoter activity in the terminator. In galactose media, the GAL1 promoter is induced and higher mStrawberry transcript levels indicates insufficient transcription termination and read-through. In FIG. 6B are the relative transcript levels of yECitrine and mStrawberry. All values are relative to the transcript level of the construct containing the CYC1 terminator in galactose. Error bars are propagated standard deviations from three technical replicates of each qPCR. Legend (left to right): CYC1, (TGuo1=SEQ ID NO: 31), (Tsynth2=SEQ ID NO:2), (Tsynth7=SEQ ID NO: 7), (Tsynth8=SEQ ID NO:8), (Tsynth10=SEQ ID NO:10), (Tsynth22=SEQ ID NO:22), (Tsynth2?=SEQ ID NO:27) and (Tsynth30=SEQ ID NO:30).

DETAILED DESCRIPTION OF THE INVENTION

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Nucleic acid as used herein also refers nucleic acids that have the same basic chemical structure as a naturally occurring nucleic acids. All sequences are written 5' to 3' unless otherwise indicated.

The terms "DNA" and "RNA" refer to deoxyribonucleic acid and ribonucleic acid, respectively. The symbols "A," "C," "T," "U," and "G" are used herein according to their standard definitions. The symbol "Y" is used herein according to its common definition in the art and refers to C or T. The symbol "W" is used herein according to its common definition in the art and refers to A or T.

"Synthetic mRNA" as used herein refers to any mRNA derived through non-natural means such as standard oligonucleotide synthesis techniques or cloning techniques (i.e. non-native mRNA or exogenous mRNA). Such mRNA may also include non-native derivatives of naturally occurring nucleotides. Additionally, "synthetic mRNA" herein also includes mRNA that has been expressed through recombinant techniques or exogenously, using any expression vehicle, including but not limited to prokaryotic cells, eukaryotic cell lines, and viral methods. "Synthetic mRNA" includes such mRNA that has been purified or otherwise obtained from an expression vehicle or system.

The words "complementary" or "complementarity" refer to the ability of a nucleic acid in a polynucleotide to form a base pair with another nucleic acid in a second polynucleotide. For example, the sequence A-G-T is complementary to the sequence T-C-A. For example, if a nucleobase at a certain position of nucleic acid is capable of hydrogen bonding with a nucleobase at a certain position of another nucleic acid, then the position of hydrogen bonding between the two nucleic acids is considered to be a complementary position. Nucleic acids are "substantially complementary" to each other when a sufficient number of complementary positions in each molecule are occupied by nucleobases that can hydrogen bond with each other. Thus, the term "substantially complementary" is used to indicate a sufficient degree of precise pairing over a sufficient number of nucleobases such that stable and specific binding occurs between the nucleic acids. The phrase "substantially complementary" thus means that there may be one or more mismatches between the nucleic acids when they are aligned, provided that stable and specific binding occurs. The term "mismatch" refers to a site at which a nucleobase in one nucleic acid and a nucleobase in another nucleic acid with which it is aligned are not complementary. The nucleic acids are "perfectly complementary" to each other when they are fully complementary across their entire length.

Where a method disclosed herein refers to "amplifying" a nucleic acid, the term "amplifying" refers to a process in which the nucleic acid is exposed to at least one round of extension, replication, or transcription in order to increase (e.g., exponentially increase) the number of copies (including complimentary copies) of the nucleic acid. The process can be iterative including multiple rounds of extension, replication, or transcription. Various nucleic acid amplification techniques are known in the art, such as PCR amplification or rolling circle amplification. Amplifying as used herein also refers to "gene synthesis" or "artificial gene synthesis" to create single-strand or double-strand polynucleotide sequences de novo using techniques known in the art.

A "primer" as used herein refers to a nucleic acid that is capable of hybridizing to a complimentary nucleic acid sequence in order to facilitate enzymatic extension, replication or transcription.

Nucleic acid is "operably linked" or "operably connected" when it is placed into a functional relationship with another nucleic acid sequence. For example, DNA for a terminator is operably linked to a coding sequence if it affects the termination of transcription of the sequence. Generally, "operably linked" means that the DNA sequences being linked are near each other, contiguous, and in reading phase.

The terms "termination sequence," "terminating sequence," or "terminator sequence" are used interchangeably herein and refer to 3' nucleic acid sequences at the end of an open reading frame that increase the propensity of release of a mRNA from the transcriptional complex. Terminator sequences may also facilitate secondary structure of mRNA or recruit termination factors.

The term "exogenous fungi transcription terminating nucleic acid sequence" refers to a non-native fungi terminating sequence having discreet sequence motifs that when 3' operably linked to a gene, modulates transcription termination of the gene. The discreet sequence motifs of an exogenous fungi transcription terminating nucleic acid sequence may independently share homology with corresponding native fungi transcription terminating sequences consensus sequences (e.g. 50%, 60%, 70% 80% 85% 90% 95%, 96%, 97%, 98%, 99%, or 100%) but have zero sequence alignment when aligned by sequence with a native fungi transcription terminating sequence.

An "efficiency nucleic acid sequence" is a nucleic acid sequence motif positioned 5' to the positioning element nucleic acid sequence, and typically signals/functions to modulate the efficiency of the transcription termination process.

A "positioning element nucleic acid sequence" is a nucleic acid motif positioned between the polyadenylation site nucleic acid sequence and the efficiency nucleic acid sequence that typically signals/functions to the location of the polyadenylation site.

A "polyadenylation site nucleic acid sequence" is a nucleic acid sequence motif positioned 3' to the positioning element nucleic acid sequence that typically signals/functions to provide a location for mRNA polyadenylation to occur.

"Heterologous" refers to a gene or its product (e.g. a mRNA) or polypeptide or protein translated from the gene product, which is not native to or otherwise typically not expressed by the host cell (e.g. fungi cell). Similarly "heterologously expressed" refers to expression of a non-native gene or gene product by a host cell (e.g. a fungi cell). A heterologous gene may be introduced into the host using techniques known in the art including, for example, transfection, transformation, or transduction.

"Homologous" refers to a gene or its product (e.g. a mRNA) or polypeptide or protein translated from the gene product, which is native to or otherwise naturally expressed by the host cell (e.g. fungi cell). Similarly "homologously expressed" refers to expression of a native gene or gene product by a host cell (e.g. a fungi cell). A homologous gene may be located in the host cell DNA (chromosome) or be introduced into the host cell using techniques known in the art included, for example, transfection and transduction.

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual*, 18.1-18.88). The level of expression of a DNA molecule may also be determined by the activity of the protein.

The terms "expression construct," "expression vector," and "expression cassette" are used interchangeably herein and in accordance with its plain ordinary meaning and refers to a polynucleotide sequence engineered to introduce particular genes into a target cell. Expression constructs described herein can be manufactured synthetically or be partially or completely of biological origin, where a biological origin includes genetically based methods of manufacture of DNA sequences.

The term "gene" means the segment of DNA involved in producing a protein or non-coding RNA; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "modulator" refers to a composition (e.g. an exogenous fungi transcription terminating nucleic acid sequence) that increases or decreases the expression of a target molecule or which increases or decreases the level of or the efficiency of transcriptional termination in a gene. Modulator may also refer to a composition which increases or decreases the expression of a non-coding RNA.

The term "modulate" is used in accordance with its plain ordinary meaning and refers to the act of changing or varying one or more properties. For example, a terminator sequence modulates the expression of a target protein changes by increasing or decreasing a property (e.g. efficiency of) associated with transcriptional termination. A terminator sequence may modulate the expression of a non-coding RNA.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "isolated" refers to a nucleic acid, polynucleotide, polypeptide, protein, or other component that is partially or completely separated from components with which it is normally associated (other proteins, nucleic acids, cells, etc.).

A "yeast cell" as used herein, refers to a eukaryotic unicellular microorganism carrying out metabolic or other function sufficient to preserve or replicate its genomic DNA. Yeast cells referenced herein include, for example, the following species: *Kluyveromyces lactis, Torulaspora delbrueckii, Zygosaccharomyces rouxii, Saccharomyces cerevisiae, Yarrowia lipolytica, Candida intermedia, Cryptococcos neoformans, Debaryomyces hansenii*, or *Scheffersomyces stipitis*. A "recombinant yeast cell" is a yeast cell which includes and/or expresses an exogenous fungi transcription terminating nucleic acid sequence described herein.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. A control as used herein may refer to the absence of an exogenous fungi transcription terminating nucleic acid sequence described herein. A control may refer to expression of a gene using a CYC1 terminator sequence (e.g. a native CYC1 terminator sequence) rather than an exogenous fungi transcription terminating nucleic acid sequence described herein. A control may also refer to comparing the level or expression or half-life of a mRNA product resulting from an exogenous fungi transcription terminating nucleic acid sequence described herein to the expression or mRNA half-life of the same gene product using SEQ ID NO:31 as the terminator.

I. Compositions

Provided herein are exogenous fungi transcription terminating nucleic acid sequences. In one aspect is an exogenous fungi transcription terminating nucleic acid sequence that includes an efficiency nucleic acid sequence of the formula $(TA)_{n1}$. The symbol n1 is an integer from 4 to 20. The exogenous fungi transcription terminating nucleic acid sequence also includes a positioning nucleic acid sequence of the formula AAWAAA, where W is A (adenosine) or T (thymidine). The exogenous fungi transcription terminating nucleic acid sequence further includes a polyadenylation site nucleic acid sequence having the sequence $(N)_{n4}Y-A_{n2}$, where the symbol N is A, C, T, or G and the symbol n4 is an integer from 0 to 10. Y is a polyadenylation site nucleotide and is C or T. The symbol n2 is an integer from 3 to 50.

W may be A. W may be T. Y may be T. Y may be C.

The symbol n1 may be 4. The symbol n1 may be 5. The symbol n1 may be 6. The symbol n1 may be 7. The symbol n1 may be 8. The symbol n1 may be 9. The symbol n1 may be 10. The symbol n1 may be 11. The symbol n1 may be 12. The symbol n1 may be 13. The symbol n1 may be 14. The symbol n1 may be 15. The symbol n1 may be 16. The symbol n1 may be 17. The symbol n1 may be 18. The symbol n1 may be 19. The symbol n1 may be 20.

The symbol n1 may be 4-18. The symbol n1 may be 4-16. The symbol n1 may be 4-15. The symbol n1 may be 4-14. The symbol n1 may be 4-12. The symbol n1 may be 4-10. The symbol n1 may be 4-8. The symbol n1 may be 4-6. The symbol n1 may be 8-18. The symbol n1 may be 8-16. The symbol n1 may be 8-15. The symbol n1 may be 8-14. The symbol n1 may be 8-12. The symbol n1 may be 8-10. The symbol n1 may be 10-20. The symbol n1 may be 10-18. The symbol n1 may be 10-16. The symbol n1 may be 10-15. The symbol n1 may be 10-14. The symbol n1 may be 10-12.

The symbol N may be C or T. The symbol N may be C. The symbol N may be T. The symbol N may be A or G. The symbol N may be A. The symbol N may be G. The symbol N may be A or T. The symbol N may be C or G.

The symbol n4 may be an integer of 0 to 3. The symbol n4 may be an integer of 0 to 3 where N is T. The symbol n4 may be an integer of 0 to 3 where N is C. The symbol n4 may be an integer of 0 to 3 where N is a combination of T and C. The symbol n4 may be an integer of 0 to 4. The symbol n4 may be an integer of 0 to 4 where N is T. The symbol n4 may be an integer of 0 to 4 where N is C. The symbol n4 may be an integer of 0 to 4 where N is a combination of T and C. The symbol n4 may be an integer of 0 to 5. The symbol n4 may be an integer of 0 to 5 where N is T. The symbol n4 may be an integer of 0 to 5 where N is C. The symbol n4 may be an integer of 0 to 5 where N is a combination of T and C. The symbol n4 may be an integer of 0 to 6. The symbol n4 may be an integer of 0 to 6 where N is T. The symbol n4 may be an integer of 0 to 6 where N is C. The symbol n4 may be an integer of 0 to 6 where N is a combination of T and C. The symbol n4 may be an integer of 0 to 7. The symbol n4 may be an integer of 0 to 7 where N is T. The symbol n4 may be an integer of 0 to 7 where N is C. The symbol n4 may be an integer of 0 to 7 where N is a combination of T and C. The symbol n4 may be an integer of 0 to 8. The symbol n4 may be an integer of 0 to 8 where N is T. The symbol n4 may be an integer of 0 to 8 where N is C. The symbol n4 may be an integer of 0 to 8 where N is a combination of T and C. The symbol n4 may be an integer of 0 to 9. The symbol n4 may be an integer of 0 to 9 where N is T. The symbol n4 may be an integer of 0 to 9 where N is C. The symbol n4 may be an integer of 0 to 9 where N is a combination of T and C. The symbol n4 may be an integer of 0 to 10 where N is T. The symbol n4 may be an integer of 0 to 10 where N is C. The symbol n4 may be an integer of 0 to 10 where N is a combination of T and C.

The symbol n4 may be an integer of 1 to 2. The symbol n4 may be an integer of 1 to 2 where N is T. The symbol n4 may be an integer of 1 to 2 where N is C. The symbol n4 may be an integer of 1 to 2 where N is a combination of T and C. The symbol n4 may be an integer of 1 to 3. The symbol n4 may be an integer of 1 to 3 where N is T. The symbol n4 may be an integer of 1 to 3 where N is C. The symbol n4 may be an integer of 1 to 3 N is a combination of T and C. The symbol n4 may be an integer of 1 to 4. The symbol n4 may be an integer of 1 to 4 where N is T. The symbol n4 may be an integer of 1 to 4 where N is C. The symbol n4 may be an integer of 1 to 4 where N is a combination of T and C. The symbol n4 may be an integer of 1 to 5. The symbol n4 may be an integer of 1 to 5 where N is T. The symbol n4 may be an integer of 1 to 5 where N is C. The symbol n4 may be an integer of 1 to 5 where N is a combination of T and C. The symbol n4 may be an integer of 1 to 6. The symbol n4 may be an integer of 1 to 6 where N is T. The symbol n4 may be an integer of 1 to 6 where N is C. The symbol n4 may be an integer of 1 to 6 where N is a combination of T and C. The symbol n4 may be an integer of 1 to 7. The symbol n4 may be an integer of 1 to 7 where N is T. The symbol n4 may be an integer of 1 to 7 where N is C. The symbol n4 may be an integer of 1 to 7 where N is a combination of T and C. The symbol n4 may be an integer of 1 to 8. The symbol n4 may be an integer of 1 to 8 where N is T. The symbol n4 may be an integer of 1 to 8 where N is C. The symbol n4 may be an integer of 1 to 8 where N is a combination of T and C. The symbol n4 may be an integer of 1 to 9. The symbol n4 may be an integer of 1 to 9 where N is T. The symbol n4 may be an integer of 1 to 9 where N is C. The symbol n4 may be an integer of 1 to 9 where N is a combination of T and C. The symbol n4 may be an integer of 1 to 10. The symbol n4 may be an integer of 1 to 10 where N is T. The symbol n4 may be an integer of 1 to 10 where N is C. The symbol n4 may be an integer of 1 to 10 where N is a combination of T and C.

The symbol n4 may be an integer of 2 to 3. The symbol n4 may be an integer of 2 to 3 where N is T. The symbol n4 may be an integer of 2 to 3 where N is C. The symbol n4 may be an integer of 2 to 3 N is a combination of T and C. The symbol n4 may be an integer of 2 to 4. The symbol n4 may be an integer of 2 to 4 where N is T. The symbol n4 may be an integer of 2 to 4 where N is C. The symbol n4 may be an integer of 2 to 4 where N is a combination of T and C. The symbol n4 may be an integer of 2 to 5. The symbol n4 may be an integer of 2 to 5 where N is T. The symbol n4 may be an integer of 2 to 5 where N is C. The symbol n4 may be an integer of 2 to 5 where N is a combination of T and C. The symbol n4 may be an integer of 2 to 6. The symbol n4 may be an integer of 2 to 6 where N is T. The symbol n4 may be an integer of 2 to 6 where N is C. The symbol n4 may be an integer of 2 to 6 where N is a combination of T and C. The symbol n4 may be an integer of 2 to 7. The symbol n4 may be an integer of 2 to 7 where N is T. The symbol n4 may be an integer of 2 to 7 where N is C. The symbol n4 may be an integer of 2 to 7 where N is a combination of T and C. The symbol n4 may be an integer of 2 to 8. The symbol n4 may be an integer of 2 to 8 where N is T. The symbol n4 may be an integer of 2 to 8 where N is C. The symbol n4 may be an integer of 2 to 8 where N is a combination of T and C. The symbol n4 may be an integer of 2 to 9. The symbol n4 may be an integer of 2 to 9 where N is T. The symbol n4 may be an integer of 2 to 9 where N is C. The symbol n4 may be an integer of 2 to 9 where N is a combination of T and C. The symbol n4 may be an integer of 2 to 10. The symbol n4 may be an integer of 2 to 10 where N is T. The symbol n4 may be an integer of 2 to 10 where N is C. The symbol n4 may be an integer of 2 to 10 where N is a combination of T and C.

The symbol n4 may be an integer of 3 to 4. The symbol n4 may be an integer of 3 to 4 where N is T. The symbol n4 may be an integer of 3 to 4 where N is C. The symbol n4 may be an integer of 3 to 4 where N is a combination of T and C. The symbol n4 may be an integer of 3 to 5. The symbol n4 may be an integer of 3 to 5 where N is T. The symbol n4 may be an integer of 3 to 5 where N is C. The symbol n4 may be an integer of 3 to 5 where N is a combination of T and C. The symbol n4 may be an integer of 3 to 6. The symbol n4 may be an integer of 3 to 6 where N is T. The symbol n4 may be an integer of 3 to 6 where N is C. The symbol n4 may be an integer of 3 to 6 where N is a combination of T and C. The symbol n4 may be an integer of 3 to 7. The symbol n4 may be an integer of 3 to 7 where N is T. The symbol n4 may be an integer of 3 to 7 where N is C. The symbol n4 may be an integer of 3 to 7 where N is a combination of T and C. The symbol n4 may be an integer of 3 to 8. The symbol n4 may be an integer of 3 to 8 where N is T. The symbol n4 may be an integer of 3 to 8 where N is C. The symbol n4 may be an integer of 3 to 8 where N is a combination of T and C. The symbol n4 may be an integer of 3 to 9. The symbol n4 may be an integer of 3 to 9 where N is T. The symbol n4 may be an integer of 3 to 9 where N is C. The symbol n4 may be an integer of 3 to 9 where N is a combination of T and C. The symbol n4 may be an integer of 3 to 10. The symbol n4 may be an integer of 3 to 10 where N is T. The symbol n4 may be an integer of 3 to 10 where N is C. The symbol n4 may be an integer of 3 to 10 where N is a combination of T and C.

The symbol n4 may be an integer of 4 to 5. The symbol n4 may be an integer of 4 to 5 where N is T. The symbol n4 may be an integer of 4 to 5 where N is C. The symbol n4 may be an integer of 4 to 5 where N is a combination of T and C. The symbol n4 may be an integer of 4 to 6. The symbol n4 may be an integer of 4 to 6 where N is T. The symbol n4 may be an integer of 4 to 6 where N is C. The symbol n4 may be an integer of 4 to 6 where N is a combination of T and C. The symbol n4 may be an integer of 4 to 7. The symbol n4 may be an integer of 4 to 7 where N is T. The symbol n4 may be an integer of 4 to 7 where N is C. The symbol n4 may be an integer of 4 to 7 where N is a combination of T and C. The symbol n4 may be an integer of 4 to 8. The symbol n4 may be an integer of 4 to 8 where N is T. The symbol n4 may be an integer of 4 to 8 where N is C. The symbol n4 may be an integer of 4 to 8 where N is a combination of T and C. The symbol n4 may be an integer of 4 to 9. The symbol n4 may be an integer of 4 to 9 where N is T. The symbol n4 may be an integer of 4 to 9 where N is C. The symbol n4 may be an integer of 4 to 9 where N is a combination of T and C. The symbol n4 may be an integer of 4 to 10. The symbol n4 may be an integer of 4 to 10 where N is T. The symbol n4 may be an integer of 4 to 10 where N is C. The symbol n4 may be an integer of 4 to 10 where N is a combination of T and C.

The symbol n4 may be 1. The symbol n4 may be 1 where N is T. The symbol n4 may be 1 where N is C. The symbol n4 may be 2. The symbol n4 may be 2 where N is T. The symbol n4 may be 2 where N is C. The symbol n4 may be 2 where N is a combination of T and C. The symbol n4 may be 3. The symbol n4 may be 3 where N is T. The symbol n4 may be 3 where N is C. The symbol n4 may be 3 where N is a combination of T and C. The symbol n4 may be 4. The symbol n4 may be 4 where N is T. The symbol n4 may be 4 where N is C. The symbol n4 may be 4 where N is a combination of T and C. The symbol n4 may be 5. The symbol n4 may be 5 where N is T. The symbol n4 may be 5 where N is C. The symbol n4 may be 5 where N is a combination of T and C. The symbol n4 may be 6. The symbol n4 may be 6 where N is T. The symbol n4 may be 6 where N is C. The symbol n4 may be 6 where N is a combination of T and C. The symbol n4 may be 7. The symbol n4 may be 7 where N is T. The symbol n4 may be 7 where N is C. The symbol n4 may be 7 where N is a combination of T and C. The symbol n4 may be 8. The symbol n4 may be 8 where N is T. The symbol n4 may be 8 where N is C. The symbol n4 may be 8 where N is a combination of T and C. The symbol n4 may be 9. The symbol n4 may be 9 where N is T. The symbol n4 may be 9 where N is C. The symbol n4 may be 9 where N is a combination of T and C. The symbol n4 may be 10. The symbol n4 may be 10 where N is T. The symbol n4 may be 10 where N is C. The symbol n4 may be 10 where N is a combination of T and C.

The symbol n2 may be an integer from 2 to 50. The symbol n2 may be an integer from 2 to 45. The symbol n2 may be an integer from 2 to 40. The symbol n2 may be an integer from 2 to 35. The symbol n2 may be an integer from 2 to 30. The symbol n2 may be an integer from 2 to 25. The symbol n2 may be an integer from 2 to 20. The symbol n2 may be an integer from 2 to 15. The symbol n2 may be an integer from 2 to 10. The symbol n2 may be an integer from 2 to 5. The symbol n2 may be an integer from 3 to 50. The symbol n2 may be an integer from 3 to 45. The symbol n2 may be an integer from 3 to 40. The symbol n2 may be an integer from 3 to 35. The symbol n2 may be an integer from 3 to 30. The symbol n2 may be an integer from 3 to 25. The symbol n2 may be an integer from 3 to 20. The symbol n2 may be an integer from 3 to 15. The symbol n2 may be an integer from 3 to 10. The symbol n2 may be an integer from 3 to 5.

The symbol n2 may be 2, 3, 4, 5, 6, 7, 8, 9, or 10. The symbol n2 may be 11, 12, 13, 14, 15, 16, 17, 18, 19, or 20. The symbol n2 may be 2. The symbol n2 may be 3. The symbol n2 may be 4. The symbol n2 may be 5. The symbol n2 may be 6. The symbol n2 may be 7. The symbol n2 may be 8. The symbol n2 may be 9. The symbol n2 may be 10. The symbol n2 may be 11. The symbol n2 may be 12. The symbol n2 may be 13. The symbol n2 may be 14. The symbol n2 may be 15. The symbol n2 may be 16. The symbol n2 may be 17. The symbol n2 may be 18. The symbol n2 may be 19. The symbol n2 may be 20.

The symbol n4 may be an integer from 1 to 5 where N is a combination of T and C and n2 is 2, 3, or 4. The symbol n4 may be an integer from 1 to 5 where N is a combination of T and C and n2 is 2. The symbol n4 may be an integer from 1 to 5 where N is a combination of T and C and n2 is 3.

The symbol n4 may be an integer from 1 to 5 and n2 may be an integer from 3 to 25. The symbol n4 may be an integer from 1 to 5 where N is a combination of T and C and n2 is an integer from 3 to 25. The symbol n4 may be an integer from 1 to 5 and n2 may be an integer from 3 to 10. The symbol n4 may be an integer from 1 to 5 where N is a combination of T and C and n2 is an integer from 3 to 10.

The symbol n4 may be an integer from 1 to 4 and n2 may be an integer from 3 to 25. The symbol n4 may be an integer from 1 to 4 where N is a combination of T and C and n2 is an integer from 3 to 25. The symbol n4 may be an integer from 1 to 4 and n2 may be an integer from 3 to 10. The symbol n4 may be an integer from 1 to 4 where N is a combination of T and C and n2 is an integer from 3 to 10.

The polyadenylation site nucleic acid sequence may have the sequence TTTCAAA (SEQ ID NO:46).

Further provided herein is an exogenous fungi transcription terminating nucleic acid sequence having the sequence $$X^1\text{-}(TA)_{n1}\text{-}L^1\text{-}AAWAAA\text{-}L^2\text{-}((N)_{n4}Y\text{-}A_{n2}). \quad \text{(Sequence I)}$$

The symbol n1 is an integer from 10-20. $X^1$ is absent or an upstream nucleic acid sequence 2 to 20 nucleotides in length. The positioning nucleic acid is as described herein. The polyadenylation site is as described herein.

$L^1$ is a first linking nucleic acid sequence linking the positioning nucleic acid sequence to the efficiency nucleic acid sequence and $L^2$ is a second linking nucleic acid sequence linking the positioning nucleic acid sequence to the polyadenylation site nucleic acid sequence. The first linking nucleic acid and second linking nucleic acid are independently 5 to 30 nucleotides in length.

The symbol n1 is as described herein. The symbol n1 may be 12. The symbols N, n4, Y, A and n2 are as described herein.

$X^1$ may be absent. $X^1$ may be an upstream nucleic acid sequence. When $X^1$ is an upstream nucleic acid sequence, $X^1$ may be an upstream nucleic acid sequence 2 to 30 nucleotides in length. $X^1$ may be an upstream nucleic acid sequence 2 to 28 nucleotides in length. $X^1$ may be an upstream nucleic acid sequence 2 to 26 nucleotides in length. $X^1$ may be an upstream nucleic acid sequence 2 to 25 nucleotides in length. $X^1$ may be an upstream nucleic acid sequence 2 to 24 nucleotides in length. $X^1$ may be an upstream nucleic acid sequence 2 to 22 nucleotides in length. $X^1$ may be an upstream nucleic acid sequence 2 to 19 nucleotides in length. $X^1$ may be an upstream nucleic acid sequence 2 to 18 nucleotides in length. $X^1$ may be an upstream nucleic acid sequence 2 to 17 nucleotides in length. $X^1$ may be an upstream nucleic acid sequence 2 to 16 nucleotides in length. $X^1$ may be an upstream nucleic acid sequence 2 to 15 nucleotides in length. $X^1$ may be an upstream nucleic acid sequence 2 to 14 nucleotides in length. $X^1$ may be an upstream nucleic acid sequence 2 to 13 nucleotides in length. $X^1$ may be an upstream nucleic acid sequence 2 to 12 nucleotides in length. $X^1$ may be an upstream nucleic acid sequence 2 to 11 nucleotides in length. $X^1$ may be an upstream nucleic acid sequence 2 to 10 nucleotides in length. $X^1$ may be an upstream nucleic acid sequence 2 to 9 nucleotides in length. $X^1$ may be an upstream nucleic acid sequence 2 to 8 nucleotides in length. $X^1$ may be an upstream nucleic acid sequence 2 to 7 nucleotides in length. $X^1$ may be an upstream nucleic acid sequence 2 to 6 nucleotides in length. $X^1$ may be an upstream nucleic acid sequence 2 to 5 nucleotides in length. $X^1$ may be an upstream nucleic acid sequence 2 to 4 nucleotides in length.

$X^1$ may be an upstream nucleic acid sequence 4 to 30 nucleotides in length. $X^1$ may be an upstream nucleic acid sequence 4 to 28 nucleotides in length. $X^1$ may be an upstream nucleic acid sequence 4 to 26 nucleotides in length. $X^1$ may be an upstream nucleic acid sequence 4 to 25 nucleotides in length. $X^1$ may be an upstream nucleic acid sequence 4 to 24 nucleotides in length. $X^1$ may be an upstream nucleic acid sequence 4 to 22 nucleotides in length. $X^1$ may be an upstream nucleic acid sequence 4 to 20 nucleotides in length. $X^1$ may be an upstream nucleic acid sequence 4 to 18 nucleotides in length. $X^1$ may be an upstream nucleic acid sequence 4 to 16 nucleotides in length. $X^1$ may be an upstream nucleic acid sequence 4 to 15 nucleotides in length. $X^1$ may be an upstream nucleic acid sequence 4 to 14 nucleotides in length. $X^1$ may be an upstream nucleic acid sequence 4 to 13 nucleotides in length. $X^1$ may be an upstream nucleic acid sequence 4 to 12 nucleotides in length. $X^1$ may be an upstream nucleic acid sequence 4 to 10 nucleotides in length. $X^1$ may be an upstream nucleic acid sequence 4 to 9 nucleotides in length. $X^1$ may be an upstream nucleic acid sequence 4 to 8 nucleotides in length. $X^1$ may be an upstream nucleic acid sequence 4 to 7 nucleotides in length. $X^1$ may be an upstream nucleic acid sequence 4 to 6 nucleotides in length.

$X^1$ may be an upstream nucleic acid sequence 6 to 30 nucleotides in length. $X^1$ may be an upstream nucleic acid sequence 6 to 28 nucleotides in length. $X^1$ may be an upstream nucleic acid sequence 6 to 26 nucleotides in length. $X^1$ may be an upstream nucleic acid sequence 6 to 25 nucleotides in length. $X^1$ may be an upstream nucleic acid sequence 6 to 24 nucleotides in length. $X^1$ may be an upstream nucleic acid sequence 6 to 22 nucleotides in length. $X^1$ may be an upstream nucleic acid sequence 6 to 20 nucleotides in length. $X^1$ may be an upstream nucleic acid sequence 6 to 18 nucleotides in length. $X^1$ may be an upstream nucleic acid sequence 6 to 16 nucleotides in length. $X^1$ may be an upstream nucleic acid sequence 6 to 15 nucleotides in length. $X^1$ may be an upstream nucleic acid sequence 6 to 14 nucleotides in length. $X^1$ may be an upstream nucleic acid sequence 6 to 13 nucleotides in length. $X^1$ may be an upstream nucleic acid sequence 6 to 12 nucleotides in length. $X^1$ may be an upstream nucleic acid sequence 6 to 11 nucleotides in length. $X^1$ may be an upstream nucleic acid sequence 6 to 10 nucleotides in length. $X^1$ may be an upstream nucleic acid sequence 6 to 9 nucleotides in length. $X^1$ may be an upstream nucleic acid sequence 6 to 8 nucleotides in length.

$X^1$ may be an upstream nucleic acid sequence 8 to 30 nucleotides in length. $X^1$ may be an upstream nucleic acid sequence 8 to 28 nucleotides in length. $X^1$ may be an upstream nucleic acid sequence 8 to 26 nucleotides in length. $X^1$ may be an upstream nucleic acid sequence 8 to 25 nucleotides in length. $X^1$ may be an upstream nucleic acid sequence 8 to 24 nucleotides in length. $X^1$ may be an upstream nucleic acid sequence 8 to 22 nucleotides in length. $X^1$ may be an upstream nucleic acid sequence 8 to 20 nucleotides in length. $X^1$ may be an upstream nucleic acid sequence 8 to 18 nucleotides in length. $X^1$ may be an upstream nucleic acid sequence 8 to 16 nucleotides in length. $X^1$ may be an upstream nucleic acid sequence 8 to 15 nucleotides in length. $X^1$ may be an upstream nucleic acid sequence 8 to 14 nucleotides in length. $X^1$ may be an upstream nucleic acid sequence 8 to 13 nucleotides in length. $X^1$ may be an upstream nucleic acid sequence 8 to 12 nucleotides in length. $X^1$ may be an upstream nucleic acid sequence 8 to 11 nucleotides in length. $X^1$ may be an upstream nucleic acid sequence 8 to 10 nucleotides in length.

The upstream nucleic acid sequence may be 5' to the efficiency nucleic acid sequence. The upstream nucleic acid sequence may be 5' to the efficiency nucleic acid sequence where the upstream nucleic acid sequence has the formula $(T)_{n3}$. The symbol n3 may be an integer from 2 to 18. The symbol n3 may be an integer from 2 to 15. The symbol n3 may be an integer from 2 to 14. The symbol n3 may be an integer from 2 to 13. The symbol n3 may be an integer from 2 to 12. The symbol n3 may be an integer from 2 to 10. The symbol n3 may be an integer from 2 to 9. The symbol n3 may be an integer from 2 to 8. The symbol n3 may be an integer from 2 to 7. The symbol n3 may be an integer from 2 to 6. The symbol n3 may be an integer from 2 to 5. The symbol n3 may be an integer from 2 to 4.

The symbol n3 may be an integer from 3 to 18. The symbol n3 may be an integer from 3 to 15. The symbol n3 may be an integer from 3 to 14. The symbol n3 may be an integer from 3 to 13. The symbol n3 may be an integer from 3 to 12. The symbol n3 may be an integer from 3 to 11. The symbol n3 may be an integer from 3 to 10. The symbol n3 may be an integer from 3 to 9. The symbol n3 may be an integer from 3 to 8. The symbol n3 may be an integer from 3 to 7. The symbol n3 may be an integer from 3 to 6. The symbol n3 may be an integer from 3 to 5.

The symbol n3 may be an integer from 4 to 18. The symbol n3 may be an integer from 4 to 15. The symbol n3 may be an integer from 4 to 14. The symbol n3 may be an integer from 4 to 13. The symbol n3 may be an integer from 4 to 12. The symbol n3 may be an integer from 4 to 11. The symbol n3 may be an integer from 4 to 10. The symbol n3 may be an integer from 4 to 9. The symbol n3 may be an integer from 4 to 8. The symbol n3 may be an integer from 4 to 7. The symbol n3 may be an integer from 4 to 6.

The symbol n3 may be an integer from 6 to 18. The symbol n3 may be an integer from 6 to 15. The symbol n3 may be an integer from 6 to 14. The symbol n3 may be an integer from 6 to 13. The symbol n3 may be an integer from 6 to 12. The symbol n3 may be an integer from 6 to 11. The symbol n3 may be an integer from 6 to 10. The symbol n3 may be an integer from 6 to 9. The symbol n3 may be an integer from 6 to 8.

The symbol n3 may be 1, 2, 3, 4, 5, 6, 7, 8, 9, 10, 11, 12, 13, 14, 15, 16, 17, 18, 19, or 20. The symbol n3 may be 1. The symbol n3 may be 2. The symbol n3 may be 3. The symbol n3 may be 4. The symbol n3 may be 5. The symbol n3 may be 6. The symbol n3 may be 7. The symbol n3 may be 8. The symbol n3 may be 9. The symbol n3 may be 10. The symbol n3 may be 11. The symbol n3 may be 12. The symbol n3 may be 13. The symbol n3 may be 14. The symbol n3 may be 15. The symbol n3 may be 16. The symbol n3 may be 17. The symbol n3 may be 18. The symbol n3 may be 19. The symbol n3 may be 20.

The upstream nucleic acid sequence may have the sequence TGGGTGGTA (SEQ ID NO:36). The upstream nucleic acid sequence may have the sequence TGGGTGG-TATGT (SEQ ID NO:38). The upstream nucleic acid sequence may have the sequence TTTTTTTT (SEQ ID NO:33). The upstream nucleic acid sequence may have a sequence set forth in Table 1.

TABLE 1

Exemplary upstream nucleic acid sequences

| Upstream Nucleic Acid Sequence | SEQ ID NO |
|---|---|
| TTTTTTTT | SEQ ID NO: 33 |
| CGCATTGGCCGGCCAATGCG | SEQ ID NO: 34 |
| AATCAAATTC | SEQ ID NO: 35 |
| TGGGTGGTA | SEQ ID NO: 36 |
| GTGGTATGT | SEQ ID NO: 37 |
| TGGGTGGTATGT | SEQ ID NO: 38 |

The first linking nucleic acid and the second linking nucleic acid may independently be 5 to 28 nucleotides in length. The first linking nucleic acid and the second linking nucleic acid may independently be 5 to 26 nucleotides in length. The first linking nucleic acid and the second linking nucleic acid may independently be 5 to 25 nucleotides in length. The first linking nucleic acid and the second linking nucleic acid may independently be 5 to 24 nucleotides in length. The first linking nucleic acid and the second linking nucleic acid may independently be 5 to 22 nucleotides in length. The first linking nucleic acid and the second linking nucleic acid may independently be 5 to 20 nucleotides in length. The first linking nucleic acid and the second linking nucleic acid may independently be 5 to 18 nucleotides in length. The first linking nucleic acid and the second linking nucleic acid may independently be 5 to 16 nucleotides in length. The first linking nucleic acid and the second linking nucleic acid may independently be 5 to 15 nucleotides in length. The first linking nucleic acid and the second linking nucleic acid may independently be 5 to 14 nucleotides in length. The first linking nucleic acid and the second linking nucleic acid may independently be 5 to 13 nucleotides in length. The first linking nucleic acid and the second linking nucleic acid may independently be 5 to 12 nucleotides in length. The first linking nucleic acid and the second linking nucleic acid may independently be 5 to 11 nucleotides in length. The first linking nucleic acid and the second linking nucleic acid may independently be 5 to 10 nucleotides in length. The first linking nucleic acid and the second linking nucleic acid may independently be 5 to 9 nucleotides in length. The first linking nucleic acid and the second linking nucleic acid may independently be 5 to 8 nucleotides in length. The first linking nucleic acid and the second linking nucleic acid may independently be 5 to 7 nucleotides in length.

The first linking nucleic acid and the second linking nucleic acid may independently be 6 to 28 nucleotides in length. The first linking nucleic acid and the second linking nucleic acid may independently be 6 to 26 nucleotides in length. The first linking nucleic acid and the second linking nucleic acid may independently be 6 to 25 nucleotides in length. The first linking nucleic acid and the second linking nucleic acid may independently be 6 to 24 nucleotides in length. The first linking nucleic acid and the second linking nucleic acid may independently be 6 to 22 nucleotides in length. The first linking nucleic acid and the second linking nucleic acid may independently be 6 to 20 nucleotides in length. The first linking nucleic acid and the second linking nucleic acid may independently be 6 to 18 nucleotides in length. The first linking nucleic acid and the second linking nucleic acid may independently be 6 to 16 nucleotides in length. The first linking nucleic acid and the second linking nucleic acid may independently be 6 to 15 nucleotides in length. The first linking nucleic acid and the second linking nucleic acid may independently be 6 to 14 nucleotides in length. The first linking nucleic acid and the second linking nucleic acid may independently be 6 to 13 nucleotides in length. The first linking nucleic acid and the second linking nucleic acid may independently be 6 to 12 nucleotides in length. The first linking nucleic acid and the second linking nucleic acid may independently be 6 to 10 nucleotides in length. The first linking nucleic acid and the second linking nucleic acid may independently be 6 to 9 nucleotides in length. The first linking nucleic acid and the second linking nucleic acid may independently be 6 to 8 nucleotides in length.

The first linking nucleic acid and the second linking nucleic acid may independently be 8 to 28 nucleotides in length. The first linking nucleic acid and the second linking nucleic acid may independently be 8 to 26 nucleotides in length. The first linking nucleic acid and the second linking nucleic acid may independently be 8 to 25 nucleotides in length. The first linking nucleic acid and the second linking nucleic acid may independently be 8 to 24 nucleotides in length. The first linking nucleic acid and the second linking nucleic acid may independently be 8 to 22 nucleotides in length. The first linking nucleic acid and the second linking nucleic acid may independently be 8 to 20 nucleotides in length. The first linking nucleic acid and the second linking nucleic acid may independently be 8 to 18 nucleotides in length. The first linking nucleic acid and the second linking nucleic acid may independently be 8 to 16 nucleotides in length. The first linking nucleic acid and the second linking nucleic acid may independently be 8 to 15 nucleotides in length. The first linking nucleic acid and the second linking nucleic acid may independently be 8 to 14 nucleotides in length. The first linking nucleic acid and the second linking nucleic acid may independently be 8 to 13 nucleotides in length. The first linking nucleic acid and the second linking nucleic acid may independently be 8 to 12 nucleotides in length. The first linking nucleic acid and the second linking nucleic acid may independently be 8 to 10 nucleotides in length.

The first linking nucleic acid and the second linking nucleic acid may independently be 1 nucleotide in length. The first linking nucleic acid and the second linking nucleic acid may independently be 2 nucleotides in length. The first linking nucleic acid and the second linking nucleic acid may independently be 3 nucleotides in length. The first linking nucleic acid and the second linking nucleic acid may independently be 4 nucleotides in length. The first linking nucleic acid and the second linking nucleic acid may independently be 5 nucleotides in length. The first linking nucleic acid and the second linking nucleic acid may independently be 6 nucleotides in length. The first linking nucleic acid and the second linking nucleic acid may independently be 7 nucleotides in length. The first linking nucleic acid and the second linking nucleic acid may independently be 8 nucleotides in length. The first linking nucleic acid and the second linking nucleic acid may independently be 9 nucleotides in length. The first linking nucleic acid and the second linking nucleic acid may independently be 10 nucleotides in length. The first linking nucleic acid and the second linking nucleic acid may independently be 11 nucleotides in length. The first linking nucleic acid and the second linking nucleic acid may independently be 12 nucleotides in length. The first linking nucleic acid and the second linking nucleic acid may independently be 13 nucleotides in length. The first linking nucleic acid and the second linking nucleic acid may independently be 14 nucleotides in length. The first linking nucleic acid and the second linking nucleic acid may independently be 15 nucleotides in length. The first linking nucleic acid and the second linking nucleic acid may independently be 16 nucleotides in length. The first linking nucleic acid and the second linking nucleic acid may independently be 17 nucleotides in length. The first linking nucleic acid and the second linking nucleic acid may independently be 18 nucleotides in length. The first linking nucleic acid and the second linking nucleic acid may independently be 19 nucleotides in length. The first linking nucleic acid and the second linking nucleic acid may independently be 20 nucleotides in length. The first linking nucleic acid and the second linking nucleic acid may independently be 22 nucleotides in length. The first linking nucleic acid and the second linking nucleic acid may independently be 24 nucleotides in length. The first linking nucleic acid and the second linking nucleic acid may independently be 26 nucleotides in length. The first linking nucleic acid and the second linking nucleic acid may independently be 28 nucleotides in length. The first linking nucleic acid and the second linking nucleic acid may independently be 30 nucleotides in length.

The first linking nucleic acid may have the sequence ACTGTCTAGA (SEQ ID NO:39). The first linking nucleic acid may have the sequence AACTCATTTACTTATGTAGG (SEQ ID NO:40). The first linking nucleic acid may have the sequence CACCCGTCGAGCCTGTCCGA (SEQ ID NO:42). The first linking nucleic acid may have the sequence GGTGCAGGCA (SEQ ID NO:43). The first linking nucleic acid may have the sequence TTT (SEQ ID NO:44). The first linking nucleic acid may have a sequence as set forth in Table 2.

The second linking nucleic acid may have the sequence GAGTATCATC (SEQ ID NO:41). The second linking nucleic acid may have the sequence AACTCATTTACTTATGTAGG (SEQ ID NO:40). The second linking nucleic acid may have the sequence CACCCGTCGAGCCTGTCCGA (SEQ ID NO:42). The second linking nucleic acid may have the sequence GGTGCAGGCA (SEQ ID NO:43). The second linking nucleic acid may have the sequence TTT (SEQ ID NO:44).

The first linking nucleic acid may have the sequence ACTGTCTAGA (SEQ ID NO:39) and $L^2$ the second linking nucleic acid may have the sequence GAGTATCATC (SEQ ID NO:41).

TABLE 2

Exemplary Linking Nucleic Acid Sequences

| Linking Nucleic Acid Sequence | SEQ ID NO |
|---|---|
| ACTGTCTAGA | SEQ ID NO: 39 |
| AACTCATTTACTTATGTAGG | SEQ ID NO: 40 |
| GAGTATCATC | SEQ ID NO: 41 |
| CACCCGTCGAGCCTGTCCGA | SEQ ID NO: 42 |
| GGTGCAGGCA | SEQ ID NO: 43 |
| TTT | SEQ ID NO: 44 |

Provided herein is an exogenous fungi transcription terminating nucleic acid sequence that includes an efficiency nucleic acid sequence of the formula $(TA)_{n1}$, where n1 is an integer from 3 to 20 and a positioning nucleic acid sequence as described herein. The exogenous fungi transcription terminating nucleic acid sequence also includes a polyadenylation site nucleic acid sequence as described herein. The exogenous fungi transcription terminating nucleic acid further includes a sequence a first linking nucleic acid sequence linking as described herein or a second linking nucleic acid sequence as described herein, where the first linking nucleic acid and the second linking nucleic acid are independently 3 to 30 nucleotides in length and consist of less than about 35% of cytosine and guanine.

The symbol n1 may be an integer of 3 to 12.

The first linking nucleic acid sequence may be 10 to 25 nucleotides in length. The first linking nucleic acid sequence may be 20 nucleotides in length.

The first linking nucleic acid sequence or the second linking nucleic acid sequence may consist of less than about 34% cytosine and guanine. The first linking nucleic acid sequence or the second linking nucleic acid sequence may consist of less than about 32% cytosine and guanine. The first linking nucleic acid sequence or the second linking nucleic acid sequence may consist of less than about 30% cytosine and guanine. The first linking nucleic acid sequence or the second linking nucleic acid sequence may consist of less than about 28% cytosine and guanine. The first linking nucleic acid sequence or the second linking nucleic acid sequence may consist of less than about 26% cytosine and guanine. The first linking nucleic acid sequence or the second linking nucleic acid sequence may consist of less than about 25% cytosine and guanine. The first linking nucleic acid sequence or the second linking nucleic acid sequence may consist of less than about 24% cytosine and guanine. The first linking nucleic acid sequence or the second linking nucleic acid sequence may consist of less than about 22% cytosine and guanine. The first linking nucleic acid sequence or the second linking nucleic acid sequence may consist of less than about 20% cytosine and guanine. The first linking nucleic acid sequence or the second linking nucleic acid sequence may consist of less than about 18% cytosine and guanine. The first linking nucleic acid sequence or the second linking nucleic acid sequence may consist of less than about 16% cytosine and guanine. The first linking nucleic acid sequence or the second linking nucleic acid sequence may consist of less than about 15% cytosine and guanine. The first linking nucleic acid sequence or the second linking nucleic acid sequence may consist of less than about 14% cytosine and guanine. The first linking nucleic acid sequence or the second linking nucleic acid sequence may consist of less than about 12% cytosine and guanine. The first linking nucleic acid sequence or the second linking nucleic acid sequence may consist of less than about 10% cytosine and guanine. The first linking nucleic acid sequence or the second linking nucleic acid sequence may consist of less than about 8% cytosine and guanine. The first linking nucleic acid sequence or the second linking nucleic acid sequence may consist of less than about 6% cytosine and guanine. The first linking nucleic acid sequence or the second linking nucleic acid sequence may consist of less than about 5% cytosine and guanine. The first linking nucleic acid sequence or the second linking nucleic acid sequence may consist of less than about 4% cytosine and guanine. The first linking nucleic acid sequence or the second linking nucleic acid sequence may consist of less than about 3% cytosine and guanine. The first linking nucleic acid sequence or the second linking nucleic acid sequence may consist of less than about 2% cytosine and guanine. The first linking nucleic acid sequence or the second linking nucleic acid sequence may consist of less than about 1% cytosine and guanine.

The first linking nucleic acid sequence and the second linking nucleic acid sequence may consist of less than about 34% cytosine and guanine. The first linking nucleic acid sequence and the second linking nucleic acid sequence may consist of less than about 32% cytosine and guanine. The first linking nucleic acid sequence and the second linking nucleic acid sequence may consist of less than about 30% cytosine and guanine. The first linking nucleic acid sequence and the second linking nucleic acid sequence may consist of less than about 28% cytosine and guanine. The first linking nucleic acid sequence and the second linking nucleic acid sequence may consist of less than about 26% cytosine and guanine. The first linking nucleic acid sequence and the second linking nucleic acid sequence may consist of less than about 25% cytosine and guanine. The first linking nucleic acid sequence and the second linking nucleic acid sequence may consist of less than about 24% cytosine and guanine. The first linking nucleic acid sequence and the second linking nucleic acid sequence may consist of less than about 22% cytosine and guanine. The first linking nucleic acid sequence and the second linking nucleic acid sequence may consist of less than about 20% cytosine and guanine. The first linking nucleic acid sequence and the second linking nucleic acid sequence may consist of less than about 18% cytosine and guanine. The first linking nucleic acid sequence and the second linking nucleic acid sequence may consist of less than about 16% cytosine and guanine. The first linking nucleic acid sequence and the second linking nucleic acid sequence may consist of less than about 15% cytosine and guanine. The first linking nucleic acid sequence and the second linking nucleic acid sequence may consist of less than about 14% cytosine and guanine. The first linking nucleic acid sequence and the second linking nucleic acid sequence may consist of less than about 12% cytosine and guanine. The first linking nucleic acid sequence and the second linking nucleic acid sequence may consist of less than about 10% cytosine and guanine. The first linking nucleic acid sequence and the second linking nucleic acid sequence may consist of less than about 8% cytosine and guanine. The first linking nucleic acid sequence and the second linking nucleic acid sequence may consist of less than about 6% cytosine and guanine. The first linking nucleic acid sequence and the second linking nucleic acid sequence may consist of less than about 5% cytosine and guanine. The first linking nucleic acid sequence and the second linking nucleic acid sequence may consist of less than about 4% cytosine and guanine. The first linking nucleic acid sequence and the second linking nucleic acid sequence may consist of less than about 3% cytosine and guanine. The first linking nucleic acid sequence and the second linking nucleic acid sequence may consist of less than about 2% cytosine and guanine. The first linking nucleic acid sequence and the second linking nucleic acid sequence may consist of less than about 1% cytosine and guanine.

Provided herein is an exogenous fungi transcription terminating nucleic acid sequence that includes an efficiency nucleic acid sequence of the formula $(TA)_{n1}$, where n1 is an integer from 3 to 20 and a positioning nucleic acid sequence as described herein. The exogenous fungi transcription terminating nucleic acid sequence further includes a polyadenylation site nucleic acid sequence as described herein. The exogenous fungi transcription terminating nucleic acid sequence further includes an upstream nucleic acid sequence having the formula $(T)_{n3}$ which is located 5' to the efficiency nucleic acid sequence. The symbol n3 is an integer from 2 to 20. The exogenous fungi transcription terminating nucleic acid sequence may further include a first linking nucleic acid sequence. The first linking nucleic acid sequence is as described herein. The exogenous fungi transcription terminating nucleic acid sequence may further include a second linking nucleic acid sequence. The second linking nucleic acid sequence is as described herein.

The symbol n1 may be as described herein. The symbol n1 may be an integer from 3 to 12. The symbol n3 may be as described herein. The symbol n3 may be an integer from 4 to 12. The symbol n3 may be an integer from 6 to 10. The symbol n3 may be 8.

The first linking nucleic acid sequence may be 3 to 30 nucleotides in length. The first linking nucleic acid sequence may be about 8 to 22 nucleotides in length. The first linking nucleic acid sequence may be about 10 nucleotides in length. The first linking nucleic acid sequence may be about 20 nucleotides in length. The first linking nucleic acid sequence may have the sequence ACTGTCTAGA (SEQ ID NO:39) or AACTCATTTACTTATGTAGG (SEQ ID NO:40).

The second linking nucleic acid sequence may be 3 to 12 nucleotides in length. The second linking nucleic acid sequence may be 3 nucleotides in length. The second linking nucleic acid sequence may be 10 nucleotides in length. The second linking nucleic acid sequence may have the sequence GAGTATCATC (SEQ ID NO:41) or TTT (SEQ ID NO:44).

The exogenous fungi transcription terminating nucleic acid sequences described herein may have a length less than about 300 nucleotides. The exogenous fungi transcription terminating nucleic acid sequences described herein may have a length less than about 250 nucleotides. The exogenous fungi transcription terminating nucleic acid sequences described herein may have a length less than about 225 nucleotides. The exogenous fungi transcription terminating nucleic acid sequences described herein may have a length less than about 200 nucleotides. The exogenous fungi transcription terminating nucleic acid sequences described herein may have a length less than about 175 nucleotides. The exogenous fungi transcription terminating nucleic acid sequences described herein may have a length less than about 150 nucleotides. The exogenous fungi transcription terminating nucleic acid sequences described herein may have a length less than about 125 nucleotides. The exogenous fungi transcription terminating nucleic acid sequences described herein may have a length less than about 100 nucleotides. The exogenous fungi transcription terminating nucleic acid sequences described herein may have a length less than about 90 nucleotides. The exogenous fungi transcription terminating nucleic acid sequences described herein may have a length less than about 80 nucleotides. The exogenous fungi transcription terminating nucleic acid sequences described herein may have a length less than about 75 nucleotides. The exogenous fungi transcription terminating nucleic acid sequences described herein may have a length less than about 70 nucleotides. The exogenous fungi transcription terminating nucleic acid sequences described herein may have a length less than about 60 nucleotides. The exogenous fungi transcription terminating nucleic acid sequences described herein may have a length less than about 50 nucleotides. The exogenous fungi transcription terminating nucleic acid sequences described herein may have a length less than about 40 nucleotides. The exogenous fungi transcription terminating nucleic acid sequences described herein may have a length less than about 35 nucleotides. The exogenous fungi transcription terminating nucleic acid sequences described herein may have a length less than about 30 nucleotides.

The exogenous fungi transcription terminating nucleic acid sequences described herein may have a length of about 30 to 300 nucleotides. The exogenous fungi transcription terminating nucleic acid sequences described herein may have a length of about 30 to 250 nucleotides. The exogenous fungi transcription terminating nucleic acid sequences described herein may have a length of about 30 to 200 nucleotides. The exogenous fungi transcription terminating nucleic acid sequences described herein may have a length of about 30 to 150 nucleotides. The exogenous fungi transcription terminating nucleic acid sequences described herein may have a length of about 30 to 100 nucleotides. The exogenous fungi transcription terminating nucleic acid sequences described herein may have a length of about 30 to 75 nucleotides. The exogenous fungi transcription terminating nucleic acid sequences described herein may have a length of about 30 to 50 nucleotides. The exogenous fungi transcription terminating nucleic acid sequences described herein may have a length of about 35 to 250 nucleotides. The exogenous fungi transcription terminating nucleic acid sequences described herein may have a length of about 35 to 200 nucleotides. The exogenous fungi transcription terminating nucleic acid sequences described herein may have a length of about 35 to 100 nucleotides. The exogenous fungi transcription terminating nucleic acid sequences described herein may have a length of about 50 to 300 nucleotides. The exogenous fungi transcription terminating nucleic acid sequences described herein may have a length of about 50 to 200 nucleotides. The exogenous fungi transcription terminating nucleic acid sequences described herein may have a length of about 50 to 100 nucleotides. The exogenous fungi transcription terminating nucleic acid sequences described herein may have a length of about 75 to 300 nucleotides. The exogenous fungi transcription terminating nucleic acid sequences described herein may have a length of about 75 to 250 nucleotides. The exogenous fungi transcription terminating nucleic acid sequences described herein may have a length of about 75 to 200 nucleotides. The exogenous fungi transcription terminating nucleic acid sequences described herein may have a length of about 75 to 150 nucleotides. The exogenous fungi transcription terminating nucleic acid sequences described herein may have a length of about 75 to 100 nucleotides.

The exogenous fungi transcription terminating nucleic acid sequences described herein may have a sequence as set forth in Table 3.

The exogenous fungi transcription terminating nucleic acid sequence may have the sequence:

(SEQ ID NO: 27)
TGGGTGGTATATATATATATATATATATATAACTGTCTAGAAATAAAG

AGTATCATCTTTCAAA.

The exogenous fungi transcription terminating nucleic acid sequence may have the sequence:

(SEQ ID NO: 29)
TGGGTGGTATGTTATATATATATATATATATATATAACTGTCTAGAAATA

AAGAGTATCATCTTTCAAA.

The exogenous fungi transcription terminating nucleic acid sequence may have the sequence:

(SEQ ID NO: 2)
TATATATATATATATATATATATAACTGTCTAGAAATAAAGAGTATCATC

TTTCAAA.

The exogenous fungi transcription terminating nucleic acid sequence may have the sequence:

(SEQ ID NO: 3)
TATATATATATATATATATATATATATATATATAACTGTCTAGAAATA

AAGAGTATCATCTTTCAAA.

The exogenous fungi transcription terminating nucleic acid sequence may have the sequence:

(SEQ ID NO: 8)
TATATAAACTCATTTACTTATGTAGGAATAAAGAGTATCATCTTTCAAA.

The exogenous fungi transcription terminating nucleic acid sequence may have the sequence:

(SEQ ID NO: 7)
TATATAACTGTCTAGAAATAAATTTTTTCAAA.

The exogenous fungi transcription terminating nucleic acid sequence may have the sequence:

(SEQ ID NO: 25)
TTTTTTTTTATATATATATATATATATATATAACTGTCTAGAAATAA

AGAGTATCATCTTTCAAA.

The exogenous fungi transcription terminating nucleic acid sequence may have the sequence:

(SEQ ID NO: 30)
TTTTTTTTTATATATATATATATATATATATAAACTCATTTACTTAT

GTAGGAATAAATTTTTTCAAA.

In embodiments, the exogenous fungi transcription terminating nucleic acid sequences described herein do not have the sequence:

(SEQ ID NO 31)
TATATAACTGTCTAGAAATAAAGAGTATCATCTTTCAAA.

II. Expression Constructs

Further provided herein is an expression construct that includes an exogenous fungi transcription terminating nucleic acid sequence. The expression construct may be a plasmid. The expression construct may be a genome. The expression construct may be an artificial chromosome. The exogenous fungi transcription terminating nucleic acid sequence may be operably linked to a 3' open reading frame of a native or non-native gene (i.e. where native and non-native refer to gene products in a fungi cell having the expression constructs described herein). The exogenous fungi transcription terminating nucleic acid sequence may increase the expression of the gene in the expression construct when compared to a control (e.g. expression using a CYC1 terminator sequence (e.g. a native CYC1 terminator sequence) or expressed using SEQ ID NO:31). The exogenous fungi transcription terminating nucleic acid sequence may increase the half-life of the expressed gene product (e.g. mRNA) from the gene when compared to a control (e.g. gene product from a gene having a CYC1 terminator sequence (e.g. a native CYC1 terminator sequence) or SEQ ID NO:31). The exogenous fungi transcription terminating nucleic acid sequence may decrease the expression of the gene in the expression construct when compared to a control (e.g. expression using a CYC1 terminator sequence (e.g. a native CYC1 terminator sequence) or expressed using SEQ ID NO:31). The exogenous fungi transcription terminating nucleic acid sequence may decrease the half-life of the expressed gene product (e.g. mRNA) from the gene compared to a control (e.g. gene product from a gene having a CYC1 terminator sequence (e.g. a native CYC1 terminator sequence) or SEQ ID NO:31).

The expression construct may contain one or more exogenous fungi transcription terminating nucleic acid sequences, which may be the same or different from each other. The expression construct may include two or more exogenous fungi transcription terminating nucleic acid sequences which modulate (i.e. increase or decrease) the expression of the gene to which each is operably linked compared to a control (e.g. expression using a CYC1 terminator sequence (e.g. a native CYC1 terminator sequence) or expressed using SEQ ID NO:31). The expression construct may include two or more exogenous fungi transcription terminating nucleic acid sequences which increase the half-life of the expressed gene product (e.g. mRNA) compared to a control (e.g. gene product from a gene having a CYC1 terminator sequence (e.g. a native CYC1 terminator sequence) or SEQ ID NO:31). The expression construct may include two or more exogenous fungi transcription terminating nucleic acid sequences which decrease the half-life of the expressed gene product (e.g. mRNA) compared to a control (e.g. gene product from a gene having a CYC1 terminator sequence (e.g. a native CYC1 terminator sequence) or SEQ ID NO:31). By incorporating one or more exogenous fungi transcription terminating nucleic acid sequences into the expression construct, the expression of genes in the expression construct can be individually (i.e. differentially) modulated or controlled.

III. Fungi Cells

Provided herein is a fungi cell that includes an exogenous fungi transcription terminating nucleic acid sequence as described herein. The fungi cell may be a yeast cell. The yeast cell may be a *Saccharomyces cerevisiae* yeast cell, a *Yarrowia lipolytica* yeast cell, a *Candida intermedia* yeast cell, a *Cryptococcos neoformans* yeast cell, a *Debaryomyces hansenii* yeast cell, a *Kluyveromyces lactis* yeast cell, a *Torulaspora delbrueckii* yeast cell, a *Zygosaccharomyces rouxii*, yeast cell or a *Scheffersomyces stipitis* yeast cell. The yeast cell may be a *Saccharomyces cerevisiae* yeast cell or a *Yarrowia lipolytica* yeast cell. The yeast cell may be a *Saccharomyces cerevisiae* yeast cell. The yeast cell may be a *Yarrowia lipolytica* yeast cell. The yeast cell may be a *Candida intermedia* yeast cell. The yeast cell may be a *Cryptococcos neoformans* yeast cell. The yeast cell may be a *Debaryomyces hansenii* yeast cell. The yeast cell may be a *Scheffersomyces stipitis* yeast cell. The yeast cell may be a *Kluyveromyces lactis* yeast cell. The yeast cell may be a *Torulaspora delbrueckii* yeast cell. The yeast cell may be a *Zygosaccharomyces rouxii* yeast cell. The exogenous fungi transcription terminating nucleic acid sequence may be located on an expression cassette or expression construct described herein.

The exogenous fungi transcription terminating nucleic acid sequence may be operably linked to a 3' open reading frame of a gene in the fungi cell. The gene may be a homologous (i.e. native) gene in the yeast cell. The exogenous fungi transcription terminating nucleic acid sequence may be operably linked to a 3' open reading frame where the sequence is operably linked to a gene in a yeast cell through a recombination event. The gene may be a heterologous (i.e. non-native) gene. In such embodiments, the exogenous fungi transcription terminating nucleic acid sequence is expressed heterologously in the fungi cell. The gene may be on the fungi cell chromosome (through, for example, a recombination event such as homologous recombination) or on an expression construct (i.e. a plasmid or yeast artificial chromosome).

The exogenous fungi transcription terminating nucleic acid sequence may increase heterologous expression of the gene in the fungi cell compared to a control (e.g. absence of the exogenous fungi transcription terminating nucleic acid sequence; expression using a CYC1 terminator sequence (e.g. a native CYC1 terminator sequence); or expression using SEQ ID NO:31). The exogenous fungi transcription terminating nucleic acid sequence may increase the mRNA half-life of a heterologously expressed gene in a fungi cell compared to a control (e.g. absence of the exogenous fungi transcription terminating nucleic acid sequence; mRNA product from a gene having a CYC1 terminator sequence (e.g. a native CYC1 terminator sequence); or mRNA product from a gene having SEQ ID NO:31).

The exogenous fungi transcription terminating nucleic acid sequence may increase homologous expression of the gene in the fungi cell compared to a control (e.g. absence of the exogenous fungi transcription terminating nucleic acid sequence; expression using a CYC1 terminator sequence (e.g. a native CYC1 terminator sequence); or expression using SEQ ID NO:31). The exogenous fungi transcription terminating nucleic acid sequence may increase the mRNA half-life of a homologously expressed gene in a fungi cell compared to a control (e.g. absence of the exogenous fungi transcription terminating nucleic acid sequence; mRNA product from a gene having a CYC1 terminator sequence (e.g. a native CYC1 terminator sequence); or mRNA product from a gene having SEQ ID NO:31).

IV. Methods of Expression

Provided herein are methods of expressing a gene in a fungi cell. In one aspect the method is a method of expressing a gene in a fungi cell by transforming a fungi cell with an expression construct that includes a gene operably linked to an exogenous fungi transcription terminating nucleic acid sequence as described herein. The method further includes allowing the cell to express the expression construct, where the exogenous fungi transcription terminating nucleic acid sequence modulates a level of transcription of the gene, thereby expressing the gene in the fungi cell. In embodiments, a fungi cell is transformed using a terminator as described herein, where the terminator is inserted into the fungi cell genome by a recombination event (e.g. homologous recombination).

The exogenous fungi transcription terminating nucleic acid sequence may increase the level of transcription of the gene compared to a control (e.g. absence of the exogenous fungi transcription terminating nucleic acid sequence; expression using a CYC1 terminator sequence (e.g. a native CYC1 terminator sequence); or expression using SEQ ID NO:31). The exogenous fungi transcription terminating nucleic acid sequence may increase the half-life of a mRNA expressed from the gene when compared to a control (e.g. absence of the exogenous fungi transcription terminating nucleic acid sequence; mRNA product from a gene having a CYC1 terminator sequence (e.g. a native CYC1 terminator sequence); or mRNA from a gene having SEQ ID NO:31).

The exogenous fungi transcription terminating nucleic acid sequence may decrease the level of transcription of the gene when compared to a control (e.g. absence of the exogenous fungi transcription terminating nucleic acid sequence; expression using a CYC1 terminator sequence (e.g. a native CYC1 terminator sequence); or expression using SEQ ID NO:31). The exogenous fungi transcription terminating nucleic acid sequence may decrease the half-life of a mRNA expressed from the gene when compared to a control (e.g. absence of the exogenous fungi transcription terminating nucleic acid sequence; mRNA product from a gene having a CYC1 terminator sequence (e.g. a native CYC1 terminator sequence); or mRNA from a gene having SEQ ID NO:31).

V. Examples

Example 1

Herein are disclosed systematically and rationally created synthetic terminators for use in yeast. These terminators offer many advantages for the heterologous expression of genes in yeast, including being short and therefore easy to clone or synthesize, having decreased homology to the native yeast genome, and being highly functional in several yeast species of industrial interest. These terminators offer initial design insight, including the best consensus elements to use, their spacing, and GC content. Furthermore, several of the synthetic terminators yield expression levels equivalent to or better than the best native terminators known to date.

Strains.

*Saccharomyces cerevisiae* strain BY4741 (Mat a; his3Δ1; leu2Δ0; met15Δ0; ura3Δ0) (EUROSCARF) and *Yarrowia lipolytica* strain PO1f (MatA, leu2-270, ura3-302, xpr2-322, axp-2) (ATCC #MYA-2613)[10] were used as the host strains in this work. *S. cerevisiae* strains were routinely propagated at 30° C. in Yeast Extract Peptone Dextrose (YPD) medium or yeast synthetic complete (YSC) medium. YPD medium is composed of 10 g/L yeast extract, 20 g/L peptone, and 20 g/L glucose. YSC medium is composed of 6.7 g/L yeast nitrogen base, 20 g/L glucose or galactose, and CSM-His supplement (MP Biomedicals, Solon, Ohio). *Y. lipolytica* strains were propagated in YSC-Leu at 30° C. This YSC medium contains CSM-Leu supplement (MP Biomedicals, Solon, Ohio). *Escherichia coli* strain DH10B was used for all cloning and plasmid propagation. DH10B was grown at 37° C. in Luria-Bertani (LB) broth supplemented with 50 µg/mL of ampicillin. *E. coli* and *S. cereviasie* strains were cultivated with 225 RPM orbital shaking *Y. lipolytica* strains were cultivated in a rotary drum (CT-7, New Brunswick Scientific) at speed seven. Yeast and bacterial strains were stored at −80° C. in 15% glycerol.

Plasmid Construction.

All plasmids used in this study were based on the vectors in Mumberg et al.[11] The TEFmut3 promoter and the yECitrine gene were cloned via PCR from plasmids described previously[6, 12]. The CYC1* terminator is the terminator from the parent plasmid[11], which was originally cloned from the D311-3A strain[13]. All other native terminators were cloned via PCR as described previously[4]. Synthetic terminators (see Table 3) were created by annealing oligos ordered from Integrated DNA Technologies. Specifically, complimentary oligos were mixed in HF PHUSION® buffer to a final concentration of 2.5 mM, heated to 98° C. for 2 minutes, then cooled to 45° C. at 0.1° C./sec. For synthetic terminators greater than 60 base-pairs in length, primers were ordered such that the forward and reverse primers overlapped by 20 base-pairs. The annealing protocol as stated above was then followed with the addition of dNTPs and HF PHUSION® polymerase to the reaction mix per the manufacturer's instructions, and a 30 minute extension step at 72° C. was added after the annealing step. Synthetic terminators were then purified using the MER-maid Spin kit (MP Biomedicals). All cloned terminators were inserted into the plasmid using the SalI and EagI restriction sites. The SalI site, in addition to the SpeI site at the beginning of the multicloning site, was also used to insert the gene yECitrine so there was only a single restriction site between the end of the gene and the terminator. To determine termination efficiency, select terminators were cloned into a plasmid with the GAL1 promoter driving yECitrine expression. Then, the mStrawberry gene and a CYC1* terminator was cloned after each terminator using the EagI and NaeI sites available. See Table 4 for primers.

TABLE 3

Synthetic terminators sequence and description

| Terminator | Sequence (5' to 3') |
|---|---|
| SEQ ID NO: 1 | TATATATATATAACTGTCTAGAAATAA AGAGTATCATCTTTCAAA |
| SEQ ID NO: 2 | TATATATATATATATATATATAACT GTCTAGAAATAAAGAGTATCATCTTTC AAA |
| SEQ ID NO: 3 | TATATATATATATATATATATATAT ATATATAACTGTCTAGAAATAAAGA GTATCATCTTTCAAA |
| SEQ ID NO: 4 | ACTGTCTAGAAATAAAGAGTATCATCT TTCAAA |
| SEQ ID NO: 5 | TATAACTGTCTAGAAATAAAGAGTATC ATCTTTCAAA |
| SEQ ID NO: 6 | TATATATTTAATAAAGAGTATCATCTT TCAAA |

TABLE 3-continued

Synthetic terminators sequence and description

| Terminator | Sequence (5' to 3') |
|---|---|
| SEQ ID NO: 7 | TATATAACTGTCTAGAAATAAATTTTT TCAAA |
| SEQ ID NO: 8 | TATATAAACTCATTTACTTATGTAGGA ATAAAGAGTATCATCTTTCAAA |
| SEQ ID NO: 9 | TATATAACTGTCTAGAAATAAAAACTC ATTTACTTATGTAGGTTTCAAA |
| SEQ ID NO: 10 | TATATACACCCGTCGAGCCTGTCCGAA ATAAAGAGTATCATCTTTCAAA |
| SEQ ID NO: 11 | TATATAACTGTCTAGAAATAAACACCC GTCGAGCCTGTCCGATTTCAAA |
| SEQ ID NO: 12 | TATATAGGTGCAGGCAAATAAAGAGTA TCATCTTTCAAA |
| SEQ ID NO: 13 | TATATAACTGTCTAGAAATAAAGGTGC AGGCATTTCAAA |
| SEQ ID NO: 14 | TATATAACTGTCTAGAAATAAAGAGTA TCATCTAAAAA |
| SEQ ID NO: 15 | TATATAACTGTCTAGAAATAAAGAGTA TCATCCAAA |
| SEQ ID NO: 16 | TATATAACTGTCTAGAAATAAAGAGTA TCATCCAAAAA |
| SEQ ID NO: 17 | TATATAACTGTCTAGAAAAAAGAGTA TCATCTTTCAAA |
| SEQ ID NO: 18 | TATATAACTGTCTAGAAATAAAGAGTA TCATCTTTCAAATTTTTTTTT |
| SEQ ID NO: 19 | TTTTTTTTTATATAACTGTCTAGAAAT AAAGAGTATCATCTTTCAAA |
| SEQ ID NO: 20 | CGCATTGGCCGGCCAATGCGTATATAA CTGTCTAGAAATAAAGAGTATCATCTT TCAAA |
| SEQ ID NO: 21 | AATCAAATTCTATATAACTGTCTAGAA ATAAAGAGTATCATCTTTCAAA |
| SEQ ID NO: 22 | TGGGTGGTATATATAACTGTCTAGAAA TAAAGAGTATCATCTTTCAAA |
| SEQ ID NO: 23 | GTGGTATGTTATATAACTGTCTAGAAA TAAAGAGTATCATCTTTCAAA |
| SEQ ID NO: 24 | TGGGTGGTATGTTATATAACTGTCTAG AAATAAAGAGTATCATCTTTCAAA |
| SEQ ID NO: 25 | TTTTTTTTTATATATATATATATAT ATATAACTGTCTAGAAATAAAGAGTAT CATCTTTCAAA |
| SEQ ID NO: 26 | AATCAAATTCTATATATATATATATAT ATATATAACTGTCTAGAAATAAAGAGT ATCATCTTTCAAA |
| SEQ ID NO: 27 | TGGGTGGTATATATATATATATATATA TATATAACTGTCTAGAAATAAAGAGTA TCATCTTTCAAA |
| SEQ ID NO: 28 | GTGGTATGTTATATATATATATATATA TATATAACTGTCTAGAAATAAAGAGTA TCATCTTTCAAA |
| SEQ ID NO: 29 | TGGGTGGTATGTTATATATATATATAT ATATATAACTGTCTAGAAATAAAGA GTATCATCTTTCAAA |

TABLE 3-continued

Synthetic terminators sequence and description

| Terminator | Sequence (5' to 3') |
|---|---|
| SEQ ID NO: 30 | TTTTTTTTTATATATATATATATAT<br>ATATAAACTCATTTACTTATGTAGGAA<br>TAAATTTTTTCAAA |
| SEQ ID NO: 31 | TATATAACTGTCTAGAAATAAAGAGTA<br>TCATCTTTCAAA |
| SEQ ID NO: 32 | TATATAACTTTTTAAAAATAAAAAAAA<br>TTTTTTTTCAAA |
| SEQ ID NO: 45 | TATATATTTTTTTTAAAATAAAAAAAA<br>TTTTCTTTCAAA |

*Y. lipolytica* plasmids were modified centromeric, replicative plasmids as described in earlier work[9]. The vector pMCS-UAS1B$_8$-hrGFP was used to create all plasmids. Synthetic terminators were prepared with annealing and extending in HF PHUSION® buffer. The native terminator regions were obtained via PCR from genomic DNA purified with the Wizard Genomic DNA Purification kit (Promega). PCR reactions were run with recommended conditions using HF PHUSION® polymerase (NEW ENGLAND BIOLABS®, Inc.). Cloned terminators were inserted into the plasmid vector via PacI and PmeI restriction sites using T4 DNA Ligase (Thermo Scientific).

Flow Cytometry.

Fluorescence from *S. cerevisiae* strains expressing the yECitrine gene and was measured using a FACS Fortessa (BD Biosciences) using a YFP fluorochrome in biological triplicate. Cells were grown to mid-log phase overnight from a starting $OD_{600}$=0.005 and 10,000 events were collected using the Fortessa for each strain. *Y. lipolytica* strains were initially propagated from individual colonies on YSC-Leu plates into 2 mL fresh YSC-Leu media. After 48 hours of incubation in a rotary drum, cultures were normalized to an $OD_{600}$ of 0.03 in 2 mL fresh YSC-Leu media. Cultures were grown 48 hrs before being harvested. To harvest, cultures were spun down at 1,000×g for 5 minutes, washed with 5 mL of ice cold water, then 100 uL of this wash was added to 1 mL of ice cold water. Fluorescence from *Y. lipolytica* expressing the hrGFP gene was measured using the GFP fluorochrome, a voltage of 319, and 10,000 events. Day to day voltage variability was mitigated by measuring all comparable strains on the same day. FlowJo (Tree Star Inc., Ashland, Oreg.) was used to analyze data and to compute mean fluorescence values.

Quantitative PCR.

The relative abundance of heterologous mRNA was determined using quantitative RT-PCR. RNA was extracted from mid-log phase cells via cell wall digest with ZYMO-LYASE™ per manufacturer's instructions coupled with the Zymo QUICK-RNA™ Miniprep Kit. For termination efficiency experiments, cells were grown in both YSC-glucose and YSC-galactose media prior to RNA extraction. cDNA was prepared using the APPLIED BIOSYSTEMS™ High Capacity Reverse Transcription Kit (Life Technologies, Carlsbad, Calif.). Primers were obtained from Integrated DNA Technologies (see Table 4 for primers). Quantitative PCR was performed on a VIIA7™ Real Time PCR System (Life Technologies) using Fast Start SYBR® Green Master Mix (Roche, Penzberg, Germany), following the manufacturer's instructions with an annealing temperature of 58° C. ALG9 was used as the reference housekeeping gene.

TABLE 4

Primers

| Primer | Target | Sequence |
|---|---|---|
| SEQ ID NO: 47 | TEFmut3 promoter | TGACTGAGCTCATAGCCTCAA AATGTTTCTACTC |
| SEQ ID NO: 48 | TEFmut3 promoter | GGCGCTACTAGTTCTAGAAAA CTTAGATTAGATTGCTATGCT TTC |
| SEQ ID NO: 49 | GAL1 promoter | CAAAGAGCTCCTAGTACGGAT TAGAAGCCG |
| SEQ ID NO: 50 | GAL1 promoter | GGCGCTACTAGTTCTAGAATC CGGGGTTTT |
| SEQ ID NO: 51 | yECitrine | GGCGCTACTAGTATGTCTAAA GGTGAAGAATTATTCACTGG |
| SEQ ID NO: 52 | yECitrine | ACGCGTCGACTTATTTGTACA ATTCATCCATACCATG |
| SEQ ID NO: 53 | mStrawberry-$T_{CYC1}$ | catcggccgATGGTGAGCAAG GGCGA |
| SEQ ID NO: 54 | mStrawberry-$T_{CYC1}$ | ttagccggcCAAATTAAAGCC TTCGAGCGTCC |
| SEQ ID NO: 55 | yECitrine qPCR | TTCTGTCTCCGGTGAAGGTGA A |
| SEQ ID NO: 56 | yECitrine qPCR | TAAGGTTGGCCATGGAACTGG CAA |
| SEQ ID NO: 57 | mStrawberry qPCR | TCAAGACCACCTACAAGGCCA AGA |
| SEQ ID NO: 58 | mStrawberry qPCR | ACAGTTCCACGATGGTGTAGT CCT |
| SEQ ID NO: 59 | ALG9 qPCR | ATCGTGAAATTGCAGGCAGCT TGG |
| SEQ ID NO: 60 | ALG9 qPCR | CATGGCAACGGCAGAAGGCAA TAA |
| SEQ ID NO: 61 | *Y. lipolytica* $T_{FEF1}$ | ccTTAATTAAGCTGCTTGTAC CTAGTGCAACCCCAGTTTGTT AAAAATTAGTAGTCAAAA |
| SEQ ID NO: 62 | *Y. lipolytica* $T_{FEF1}$ | gcgccGTTTAAACACTGAGTG ACAGAGCCCTCTCATGTTTGG AGAGAAGACTAAGTACAA |
| SEQ ID NO: 63 | *Y. lipolytica* $T_{CYC1}$ | ccTTAATTAAGCGTCTACAAC TGGACCCTTAGCCTGTATATA TCAATTGATTATTTAAAG |
| SEQ ID NO: 64 | *Y. lipolytica* $T_{CYC1}$ | gcgccGTTTAAACGACGCAAG AGAAGCCGTCGCCCCACGGAG TATC |

Example 2

Figure 1A:
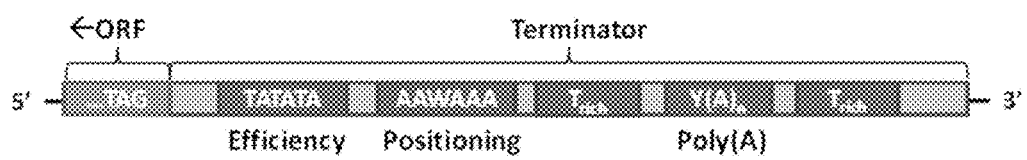
FIG. 1A depicts a general diagram of a yeast terminator.
Figure 1B:
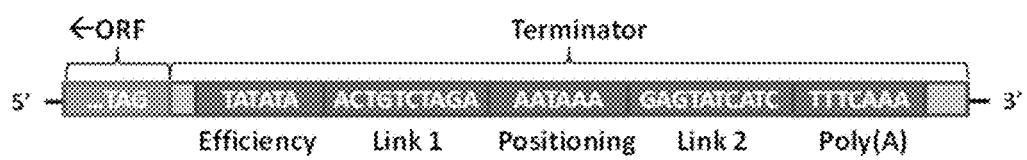
FIG. 1B depicts a diagram of a synthetic (exogenous) terminator from Guo et al. Sequence: SEQ ID NO:31.
Figure 1C:
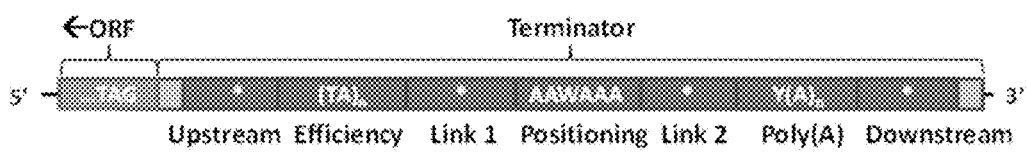
FIG. 1C depicts a diagram of synthetic (exogenous) terminators herein.

Native terminators have been well-studied in *S. cerevisiae*[2]. Several important consensus elements are known, including an efficiency element, positioning element, the polyadenylation (poly(A)) site, and T-rich regions surrounding the poly(A) site (FIG. 1A). Using these known elements, Guo et al. previously demonstrated a synthetic, minimum sequence able to achieve termination and create mature mRNA in yeast (FIG. 1B).[5] However, Guo did not compare this sequence to native terminators used in a heterologous context. We designed synthetic terminators de novo using the fundamental consensus sites required for termination. Variants of each site and spacer region were explored to determine the sequence elements important for protein expression level and termination efficiency (FIG. 1C). Several sequences identified in this work perform as well as or better than the best native sequences previously reported.[4] One synthetic terminator resulted in 3.5-fold more protein production than the commonly used CYC1 terminator, and 1.6-fold more than the synthetic sequence defined by Guo et al. Additionally, several of the synthetic designs were tested in the alternative yeast *Yarrowia lipolytica*. Of these synthetic terminators, several resulted in as much protein production as native *Y. lipolytica* terminators, demonstrating that these synthetic designs are transferable between diverse yeast species.

Experimental.

The first synthetic terminator in yeast was described by Guo et al.[5] in 1996 (herein SEQ ID NO:31 or "$T_{Guo1}$"). This terminator was designed to determine the minimal terminator elements needed to make mature polyadenylated transcript. It was determined that the combination of the consensus sequences for the efficiency element, positioning element, and poly(A) site, spaced 10 base-pairs apart, was sufficient to make mature transcript. However, the relative abundance of this transcript or the corresponding protein compared to that created using a native terminator was not measured, and no subsequent work has been done in this area since.

We cloned $T_{Guo1}$ into a heterologous expression construct consisting of the TEFmut3 promoter[6] and the yECitrine gene for yellow fluorescent protein expression. Then, variants of the synthetic terminator were created in the same heterologous background. Many of these variants were based on elements that were identified in native terminators that are known to provide mRNA transcripts with relatively long half-lives and increased relative protein abundance[4]. For example, these include native terminators with extended efficiency elements (including the SPG5 and HIS5 terminators) or poly(T) tracts before or after the poly(A) site (including the CPS1 and IDP1 terminators). In addition, each element and spacer region was rationally altered to explore the potential effect on transcript and protein expression. These variations included alternate consensus sites for the positioning and poly(A) elements, alterations in spacer region length and % GC content, and the addition of upstream and downstream sequences (Table 1).

Example 3

Figure 2:
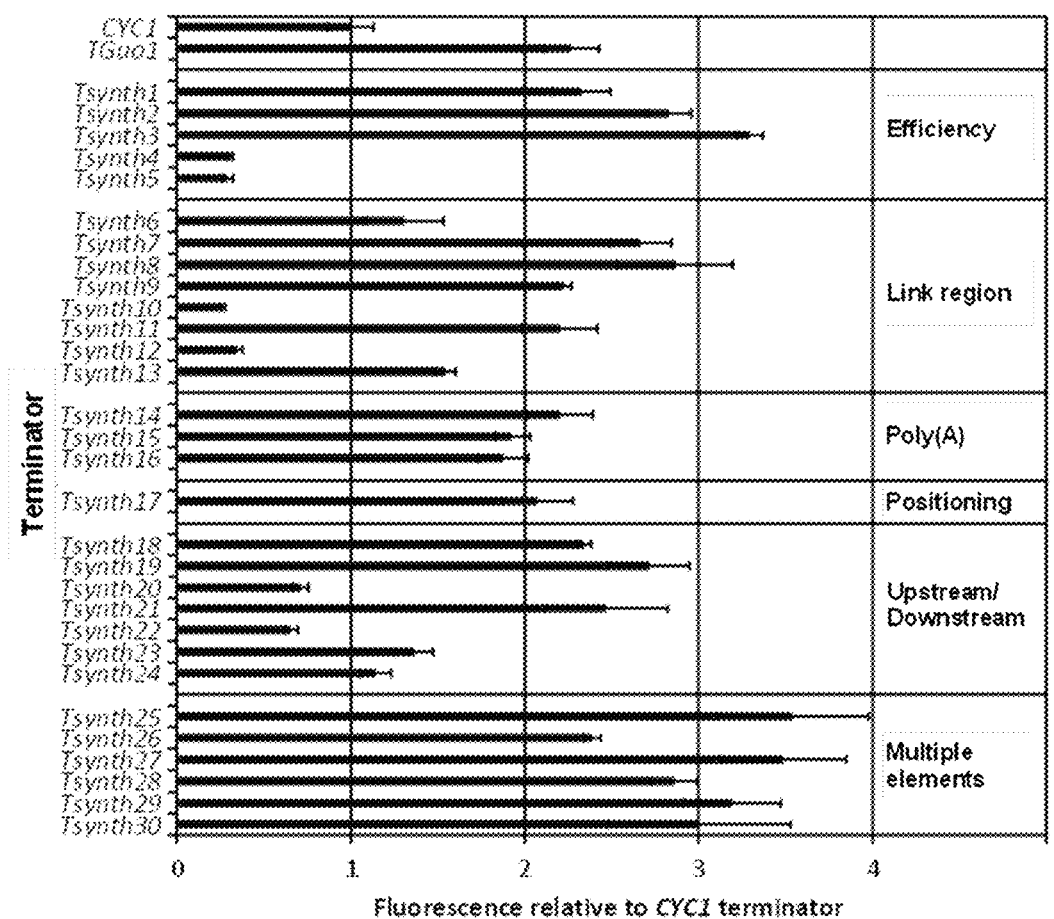
FIG. 2 depicts a histogram showing fluorescence of yellow fluorescent protein produced from heterologous expression constructs containing synthetic (exogenous) terminators. Values are relative to the CYC1 terminator, the standard terminator available in the plasmids described in Mumberg et al. Terminators are divided into categories based on the terminator element that was varied in comparison to the $T_{Guo1}$ terminator (SEQ ID NO:31). See Table 3 for terminator sequences. Tsynth1=SEQ ID NO:1. Tsynth2=SEQ ID NO:2. Tsynth3=SEQ ID NO:3. Tsynth4=SEQ ID NO:4. Tsynth5=SEQ ID NO:5. Tsynth6=SEQ ID NO:6. Tsynth7=SEQ ID NO:7. Tsynth8=SEQ ID NO:8. Tsynth9=SEQ ID NO:9. Tsynth10=SEQ ID NO:10. Tsynth11=SEQ ID NO:11. Tsynth12=SEQ ID NO:12. Tsynth13=SEQ ID NO:13.

Heterologous protein expression from genes utilizing minimal synthetic terminators. Once cloned into the with the TEFmut3 promoter and yECitrine gene, the synthetic terminators were evaluated on the basis of fluorescence via flow cytometry (FIG. 2).

$T_{Guo1}$ provides a greater level of expression when compared to the native CYC1 terminator. This terminator is 39-base pairs long and provides for expression of a heterologous gene, as described previously. The synthetic terminators surprisingly resulted in s with significantly higher or lower expression levels than $T_{Guo1}$. One set of synthetic terminators have altered length of the efficiency element, $(TA)_n$. There is clear correlation between the increased protein expression and efficiency element length (FIG. 3). Furthermore, it is clear that a minimum efficiency element length of 6 bp (TATATA) appears needed for function, as terminators with elements shorter than this length (SEQ ID NO:4 and SEQ ID NO:5) had severely decreased fluorescence.

Additional synthetic terminators alter the length and GC content of the link regions between the consensus elements. In general, link regions with greater GC content (SEQ ID NO:10-SEQ ID NO:13) were detrimental to protein expression. Synthetic terminators having linkers with lower GC content increased protein expression. A short T-rich sequence of only 3 bp for the first linker (SEQ ID NO:6) appears detrimental to protein expression. A 20 bp sequence of low GC content (30%) for the first linker (SEQ ID NO:8) surprisingly increased protein expression relative to $T_{Guo1}$. The spacing and GC content of the link regions between terminator elements appears critical to expression levels— especially between the efficiency and positioning element.

Next, several synthetic terminators with varying positioning and poly(A) sites were tested. In general, these varied regions did not have a significant effect on protein expression in the tested synthetic terminators. However, these varied regions may be useful for other purposes. For example, there may be advantages to the varied sequences to keep homology between different terminators low and prevent undesirable homologous recombination. These synthetic terminators resulted in slight decreases of expression compared to the $T_{Guo}$ sequence but still greater expression than the native terminator CYC1 (SEQ ID NO:15 and SEQ ID NO:16).

Other synthetic terminators were tested using varied upstream (5') and downstream (3') sequences of the terminators elements. First poly(T) tracts were added in either location. The addition of poly(T) tracts proved slightly beneficial for the 5' location, but no change was seen for the 3' location. In addition to the poly(T) tract, a stem loop was tested in the 5' region on the theory that the resulting 3'UTR would be more difficult to degrade and therefore result in a higher half-life. However, this element proved detrimental to expression (SEQ ID NO:20). While this particular stem loop did not increase protein expression, an analysis of the minimum energy of folding of the terminator sequences showed that there is a correlation between protein expression and the loop free-energy decomposition as predicted by mfold (FIG. 4).[7]

Other elements identified in a global bioinformatics study[8] were tested in the 5' region. These elements were identified to occur in the first 20 base pairs of several terminators that were associated with genes that had high reported mRNA half-life. Elements outside this range were excluded due to the difficulty in determining the correct placement in these short, minimal terminators. Interestingly, several of these elements resulted in lower expression overall when placed in the base construct (SEQ ID NO:22-SEQ ID NO:24) but higher expression overall when placed in a terminator with an extended efficiency element (SEQ ID NO:27-SEQ ID NO:29). Therefore, without being bound by any particular theory, these elements may need to be spaced appropriately relative to the other elements in the terminator. A combination of the best individual elements from each category (SEQ ID NO:30) did not increase protein expression further, indicating that the elements are not necessarily additive or that the variants have reached a local maximum in the optimization of the explored sequence space. Thus, the combinations may be useful in tuning the expression of particular genes in a cassette.

Example 4

Transcription termination efficiency of synthetic terminators. In addition to ensuring high levels of protein expression through mRNA stability, terminators also need to be able to ensure full transcription termination and disengagement of RNA polymerase II. This is especially important when multiple heterologous genes are cloned in series and differential induction is required, as may often be the case for metabolic engineering applications. As such, several of the synthetic terminators designed in this work were tested for termination efficiency. To do so, an additional gene (mStrawberry, encoding a red fluorescent protein) was cloned after the terminator (3'). In these constructs, the terminator was still placed at the 3' end of the yECitrine gene, and the promoter was changed to the inducible GAL1 promoter. To test termination efficiency, the transcript level of both yECitrine and mStrawberry was measured in both the induced and repressed states. In the repressed state, mStrawberry transcription is likely due to cryptic promoter activity in the terminator and surrounding sequence. In the induced state, any additional mStrawberry transcription over what was seen in the repressed state is likely due to "read-through" or incomplete transcription termination. As a comparison, several native terminators were also compared using this scheme (FIG. 5). The synthetic terminators demonstrated enhanced termination when compared to the native CYC1 sequence—a commonly used terminator sequence in metabolic engineering application.

Example 4. Synthetic Terminator Use in Alternative Yeast Hosts

The termination process is well studied in *S. cerevisiae*. Without being bound by any particular theory the termination process is likely similar in other yeast. Consequently, we sought to test several synthetic terminators in the oleaginous yeast *Yarrowia lipolytica* (a highly different yeast compared to *S. cerevisiae*) to see whether they could be used across species. The terminators were cloned into a heterologous expression construct expressing the green fluorescent protein gene hrGFP with the tef1 hybrid promoter containing eight UAS1B repeats[9]. As a comparison, the CYC1 terminator from *S. cerevisiae* and the TEF1 and CYC1 terminators from *Y. lipolytica* were also included where the TEF1 and CYC1 terminators from *Y. lipolytica* were assumed to be the 250 bp immediately following the gene open reading frame (FIG. 6). Overall, the synthetic terminators performed better than the native *S. cerevisiae* terminator and as well as the best native *Y. lipolytica* terminator. This demonstrates that synthetic terminators can be highly functional across species and will therefore allow for simplified testing of heterologous constructs in multiple yeast hosts.

REFERENCES

1. Russo, P.; Li, W. Z.; Hampsey, D. M.; Zaret, K. S.; Sherman, F., Distinct cis-acting signals enhance 3' endpoint formation of CYC1 mRNA in the yeast *Saccharomyces cerevisiae*. The EMBO journal 1991, 10 (3), 563-71; 2. Mischo, H. E.; Proudfoot, N. J., Disengaging polymerase: Terminating RNA polymerase II transcription in budding yeast. Biochimica et Biophysica Acta (BBA)—Gene Regulatory Mechanisms 2013, 1829 (1), 174-185; 3. O'Sullivan, J. M.; Tan-Wong, S. M.; Morillon, A.; Lee, B.; Coles, J.; Mellor, J.; Proudfoot, N. J., Gene loops juxtapose promoters and terminators in yeast. Nat Genet 2004, 36 (9), 1014-8; 4. Curran, K. A.; Karim, A. S.; Gupta, A.; Alper, H. S., Use of expression-enhancing terminators in *Saccharomyces cerevisiae* to increase mRNA half-life and improve gene expression control for metabolic engineering applications. Metabolic engineering 2013, 19, 88-97; 5. Guo, Z. J.; Sherman, F., Signals sufficient for 3'-end formation of yeast mRNA. Mol. Cell. Biol. 1996, 16 (6), 2772-2776; 6. (a) Alper, H.; Fischer, C.; Nevoigt, E.; Stephanopoulos, G., Tuning genetic control through promoter engineering. Proc. Natl. Acad. Sci. U.S.A. 2005, 102 (36), 12678-12683; (b) Nevoigt, E.; Kohnke, J.; Fischer, C. R.; Alper, H.; Stahl, U.; Stephanopoulos, G., Engineering of promoter replacement cassettes for fine-tuning of gene expression in *Saccharomyces cerevisiae*. Appl. Environ. Microbiol. 2006, 72 (8), 5266-5273; 7. Zuker, M., Mfold web server for nucleic acid folding and hybridization prediction. Nucleic acids research 2003, 31 (13), 3406-15; 8. Shalgi, R.; Lapidot, M.; Shamir, R.; Pilpel, Y., A catalog of stability-associated sequence elements in 3' UTRs of yeast mRNAs. Genome biology 2005, 6 (10), R86; 9. Blazeck, J.; Reed, B.; Garg, R.; Gerstner, R.; Pan, A.; Agarwala, V.; Alper, H., Generalizing a hybrid synthetic promoter approach in *Yarrowia lipolytica*. Appl Microbiol Biotechnol 2013, 97 (7), 3037-3052; 10. Madzak, C.; Treton, B.; Blanchin-Roland, S., Strong hybrid promoters and integrative expression/secretion vectors for quasi-constitutive expression of heterologous proteins in the yeast *Yarrowia lipolytica*. Journal of molecular microbiology and biotechnology 2000, 2 (2), 207-16; 11. Mumberg, D.; Muller, R.; Funk, M., Yeast vectors for the controlled expression of heterologous proteins in different genetic backgrounds. Gene 1995, 156 (1), 119-122; 12. Sheff, M. A.; Thorn, K. S., Optimized cassettes for fluorescent protein tagging in *Saccharomyces cerevisiae*. Yeast 2004, 21 (8), 661-670; 13. Montgomery, D. L.; Hall, B. D.; Gillam, S.; Smith, M., Identification and isolation of the yeast cytochrome c gene. Cell 1978, 14 (3), 673-680.

VI. Embodiments

Embodiment 1

An exogenous fungi transcription terminating nucleic acid sequence including: (i) an efficiency nucleic acid sequence of the formula $(TA)_{n1}$, wherein n1 is an integer from 4 to 20; (ii) a positioning nucleic acid sequence of the formula AAWAAA, wherein W is A or T; and (iii) a polyadenylation site nucleic acid sequence including the sequence $(N)_{n4}Y-A_{n2}$, wherein N is A, C, T, or G; n4 is an integer from 0 to 10; Y is a polyadenylation site nucleotide and is C or T; and n2 is an integer from 3 to 50.

Embodiment 2

The exogenous fungi transcription terminating nucleic acid sequence of embodiment 1, wherein n1 is 4-15.

Embodiment 3

The exogenous fungi transcription terminating nucleic acid sequence of either embodiment 1 or 2, wherein n1 is 4-12.

Embodiment 4

The exogenous fungi transcription terminating nucleic acid sequence of any one of embodiments 1-3, wherein n1 is 10-14.

Embodiment 5

The exogenous fungi transcription terminating nucleic acid sequence of any one of embodiments 1-4, wherein n1 is 12.

Embodiment 6

The exogenous fungi transcription terminating nucleic acid sequence of any one of embodiments 1-5, wherein n1 is 4-6.

Embodiment 7

An exogenous fungi transcription terminating nucleic acid sequence of embodiment 1 including the sequence: $X^1$-(TA)n1-$L^1$-AAWAAA-$L^2$-$((N)_{n4}Y-A_{n2})$ (Sequence I), wherein n1 is an integer from 10-20; $X^1$ is absent or an upstream nucleic acid sequence 2 to 20 nucleotides in length; AAWAAA is the positioning nucleic acid sequence; $(N)_{n4}Y-A_{n2}$ is the polyadenylation site nucleic acid sequence; $L^1$ is a first linking nucleic acid sequence linking the positioning nucleic acid sequence to the efficiency nucleic acid sequence and $L^2$ is a second linking nucleic acid sequence linking the positioning nucleic acid sequence to the polyadenylation site nucleic acid sequence, wherein the first linking nucleic acid sequence and the second linking nucleic acid sequence are independently 5 to 30 nucleotides in length.

Embodiment 8

The exogenous fungi transcription terminating nucleic acid sequence of embodiment 7, wherein $X^1$ is an upstream nucleic acid sequence 6 to 12 nucleotides in length.

Embodiment 9

The exogenous fungi transcription terminating nucleic acid sequence of either embodiment 7 or 8, wherein $X^1$ is an upstream nucleic acid sequence 8 to 10 nucleotides in length.

Embodiment 10

The exogenous fungi transcription terminating nucleic acid sequence of any one of embodiments 7-9, wherein $X^1$ is an upstream nucleic acid sequence is TGGGTGGTA (SEQ ID NO:36).

Embodiment 11

The exogenous fungi transcription terminating nucleic acid sequence of any one of embodiments 7-10, wherein $X^1$ is an upstream nucleic acid sequence is TGGGTGGTATGT (SEQ ID NO:38).

Embodiment 12

The exogenous fungi transcription terminating nucleic acid sequence of any one of embodiments 7-11, wherein $X^1$ is absent.

Embodiment 13

The exogenous fungi transcription terminating nucleic acid sequence of one of embodiments 7 to 12, wherein n1 is 12.

Embodiment 14

The exogenous fungi transcription terminating nucleic acid sequence of one of embodiments 7 to 13, wherein W is T.

Embodiment 15

The exogenous fungi transcription terminating nucleic acid sequence of one of embodiments 7 to 14, wherein $L^1$ and $L^2$ are independently 6 to 14 nucleotides in length.

Embodiment 16

The exogenous fungi transcription terminating nucleic acid sequence of one of embodiments 7 to 15, wherein $L^1$ and $L^2$ are independently 8 to 12 nucleotides in length.

Embodiment 17

The exogenous fungi transcription terminating nucleic acid sequence of one of embodiments 7 to 16, wherein $L^1$ and $L^2$ are independently 10 nucleotides in length.

Embodiment 18

The exogenous fungi transcription terminating nucleic acid sequence of one of embodiments 7 to 17, wherein $L^1$ is ACTGTCTAGA (SEQ ID NO:39) and $L^2$ is GAGTATCATC (SEQ ID NO:41).

Embodiment 19

The exogenous fungi transcription terminating nucleic acid sequence of one of embodiments 7 to 18, wherein n4 is an integer from 1 to 5 and n2 is an integer from 3 to 25.

Embodiment 20

The exogenous fungi transcription terminating nucleic acid sequence of one of embodiments 7 to 19, wherein n4 is an integer from 1 to 4 nucleotides and n2 is an integer from 3 to 10.

Embodiment 21

The exogenous fungi transcription terminating nucleic acid sequence of one of embodiments 7 to 20, wherein the polyadenylation site nucleic acid sequence is TTTCAAA (SEQ ID NO:46).

Embodiment 22

The exogenous fungi transcription terminating nucleic acid sequence of embodiment 7 including the sequence:

(SEQ ID NO: 27)
TGGGTGGTATATATATATATATATATATATATATAACTGTCTAGAAATA
AAGAGTATCATCTTTCAAA.

Embodiment 23

The exogenous fungi transcription terminating nucleic acid sequence of embodiment 7 including the sequence:

(SEQ ID NO: 29)
TGGGTGGTATGTTATATATATATATATATATATATAACTGTCTAGAA
ATAAAGAGTATCATCTTTCAAA.

Embodiment 24

The exogenous fungi transcription terminating nucleic acid sequence of embodiment 7 including the sequence:

(SEQ ID NO: 2)
TATATATATATATATATATATATAACTGTCTAGAAATAAAGAGTATC
ATCTTTCAAA.

Embodiment 25

The exogenous fungi transcription terminating nucleic acid sequence of embodiment 7 including the sequence:

(SEQ ID NO: 3)
TATATATATATATATATATATATATATATATATAACTGTCTAGAA
ATAAAGAGTATCATCTTTCAAA.

Embodiment 26

An exogenous fungi transcription terminating nucleic acid sequence including (i) an efficiency nucleic acid sequence of the formula $(TA)_{n1}$, wherein n1 is an integer from 3 to 20; (ii) a positioning nucleic acid sequence of the formula AAWAAA, wherein W is A or T; (iii) a polyadenylation site nucleic acid sequence including the sequence $(N)_{n4}Y\text{-}A_{n2}$, wherein N is A, C, T, or G; n4 is an integer from 0 to 10; Y is a polyadenylation site nucleotide and is C or T; and n2 is an integer from 3 to 50; and (iv) a first linking nucleic acid sequence linking the positioning nucleic acid sequence to the efficiency nucleic acid sequence or a second linking nucleic acid sequence linking the positioning nucleic acid sequence to the polyadenylation site nucleic acid sequence, wherein the first linking nucleic acid sequence and the second linking nucleic acid sequence are independently 3 to 30 nucleotides in length and consist of less than about 35% of cytosine and guanine.

Embodiment 27

The exogenous fungi transcription terminating nucleic acid sequence of embodiment 26, wherein the first linking nucleic acid sequence or the second linking nucleic acid sequence consists of less than about 30% cytosine and guanine.

Embodiment 28

The exogenous fungi transcription terminating nucleic acid sequence of either embodiment 26 or 27, wherein the first linking nucleic acid sequence or the second linking nucleic acid sequence consists of less than about 25% of cytosine and guanine.

Embodiment 29

The exogenous fungi transcription terminating nucleic acid sequence of any one of embodiments 26-28, wherein the first linking nucleic acid sequence or the second linking nucleic acid sequence consists of less than about 20% of cytosine and guanine.

Embodiment 30

The exogenous fungi transcription terminating nucleic acid sequence of any one of embodiments 26 to 29, wherein the first linking nucleic acid sequence is about 10-25 nucleotides in length.

Embodiment 31

The exogenous fungi transcription terminating nucleic acid sequence of any one of embodiments 26 to 30, wherein the first linking nucleic acid sequence is about 20 nucleotides in length.

Embodiment 32

The exogenous fungi transcription terminating nucleic acid sequence of embodiment 26 including the sequence:

(SEQ ID NO: 8)
TATATAAACTCATTTACTTATGTAGGAATAAAGAGTATCATCTTTCA
AA.

Embodiment 33

The exogenous fungi transcription terminating nucleic acid sequence of embodiment 26 including the sequence:

(SEQ ID NO: 7)
TATATAACTGTCTAGAAATAAATTTTTTCAAA.

Embodiment 34

An exogenous fungi transcription terminating nucleic acid sequence including (i) an efficiency nucleic acid sequence of the formula $(TA)_{n1}$, wherein n1 is an integer from 3 to 20; (ii) a positioning nucleic acid sequence of the formula AAWAAA, wherein W is A or T; (iii) a polyadenylation site nucleic acid sequence including the sequence $(N)_{n4}Y\text{-}A_{n2}$, wherein N is A, C, T, or G; n4 is an integer from 0 to 10; Y is a polyadenylation site nucleotide and is C or T; and n2 is an integer from 3 to 50. (iv) an upstream nucleic acid sequence 5' to the efficiency nucleic acid sequence of the formula $(T)n3$, wherein n3 is an integer from 2 to 20.

Embodiment 35

The exogenous fungi transcription terminating nucleic acid sequence of embodiment 34, wherein n1 is an integer of 3 to 12.

Embodiment 36

The exogenous fungi transcription terminating nucleic acid sequence of any one of embodiments 34 to 35, wherein W is T.

Embodiment 37

The exogenous fungi transcription terminating nucleic acid sequence of any one of embodiments 34 to 36, wherein n3 is an integer from 4 to 12.

Embodiment 38

The exogenous fungi transcription terminating nucleic acid sequence of any one of embodiments 34 to 37, wherein n3 is an integer from 6 to 10.

Embodiment 39

The exogenous fungi transcription terminating nucleic acid sequence of any one of embodiments 34 to 38, wherein n3 is 8.

Embodiment 40

The exogenous fungi transcription terminating nucleic acid sequence of any one of embodiments 34 to 39, further including a first linking nucleic acid sequence linking the positioning nucleic acid sequence to the efficiency nucleic acid sequence.

Embodiment 41

The exogenous fungi transcription terminating nucleic acid sequence of embodiment 40, wherein the first linking nucleic acid sequence is about 3 to 30 nucleotides in length.

Embodiment 42

The exogenous fungi transcription terminating nucleic acid sequence of any one of embodiments 40 to 41, wherein the first linking nucleic acid sequence is about 8 to about 22 nucleotides in length.

Embodiment 43

The exogenous fungi transcription terminating nucleic acid sequence of any one of embodiments 40 to 42, wherein the first linking nucleic acid sequence is about 10 nucleotides in length.

Embodiment 44

The exogenous fungi transcription terminating nucleic acid sequence of any one of embodiments 40 to 42, wherein the first linking nucleic acid sequence is about 20 nucleotides in length.

Embodiment 45

The exogenous fungi transcription terminating nucleic acid sequence of any one of embodiments 40-44, wherein the first linking nucleic acid sequence includes the sequence ACTGTCTAGA (SEQ ID NO:39) or AACTCATTTACT-TATGTAGG (SEQ ID NO:40).

Embodiment 46

The exogenous fungi transcription terminating nucleic acid sequence of any one of embodiments 34 to 39, further including a second linking nucleic acid sequence linking the positioning nucleic acid sequence to the polyadenylation site nucleic acid sequence.

Embodiment 47

The exogenous fungi transcription terminating nucleic acid sequence of embodiment 46, wherein the second linking nucleic acid sequence is about 3 to about 12 nucleotides in length.

Embodiment 48

The exogenous fungi transcription terminating nucleic acid sequence of any one of embodiments 46 to 47, wherein the second linking nucleic acid sequence is about 3 nucleotides in length.

Embodiment 49

The exogenous fungi transcription terminating nucleic acid sequence of any one of embodiments 46 to 47, wherein the second linking nucleic acid sequence is about 10 nucleotides in length.

Embodiment 50

The exogenous fungi transcription terminating nucleic acid sequence of any one of embodiments 46-49, wherein the second linking nucleic acid sequence includes the sequence TTT (SEQ ID NO:44) or GAGTATCATC (SEQ ID NO:41).

Embodiment 51

The exogenous fungi transcription terminating nucleic acid sequence of embodiment 34 including the sequence

```
                                    (SEQ ID NO: 25)
TTTTTTTTTATATATATATATATATATATATATAACTGTCTAGAAATAA
AGAGTATCATCTTTCAAA.
```

Embodiment 52

The exogenous fungi transcription terminating nucleic acid sequence of embodiment 34 including the sequence

```
                                    (SEQ ID NO: 30)
TTTTTTTTTATATATATATATATATATATATATAAACTCATTTACTTAT
GTAGGAATAAATTTTTTCAAA.
```

Embodiment 53

The exogenous fungi transcription terminating nucleic acid sequence of any one of embodiments 1 to 52, wherein the exogenous fungi transcription terminating nucleic acid sequence includes a length of less than about 200 nucleotides.

Embodiment 54

The exogenous fungi transcription terminating nucleic acid sequence of any one of embodiments 1 to 53, wherein the exogenous fungi transcription terminating nucleic acid sequence is not TATATAACTGTCTAGAAATAAAGAG-TATCATCTTTCAAA (SEQ ID NO:31).

Embodiment 55

A fungi cell including an exogenous fungi transcription terminating nucleic acid sequence of any one of embodiments 1 to 54.

Embodiment 56

The fungi cell of embodiment 55, wherein the exogenous fungi transcription terminating nucleic acid sequence is operably linked to a 3' open reading frame of a gene in the fungi cell.

Embodiment 57

The fungi cell of any one of embodiments 55 or 56, wherein the exogenous fungi transcription terminating nucleic acid sequence is expressed heterologously.

Embodiment 58

The fungi cell of embodiment 57, wherein the exogenous fungi transcription terminating nucleic acid sequence increases heterologous expression in the fungi cell compared to a control.

Embodiment 59

The fungi cell of embodiment 55, wherein the exogenous fungi transcription terminating nucleic acid sequence is expressed homologously.

Embodiment 60

The fungi cell of any one of embodiments 55 or 56, wherein the exogenous fungi transcription terminating nucleic acid sequence increases expression of a native fungi gene in the fungi cell compared to a control.

Embodiment 61

The fungi cell of any one of embodiments 55 to 60, wherein the fungi cell is a yeast cell.

Embodiment 62

The fungi cell of any one of embodiments 55 to 61, wherein the fungi cell is a *Saccharomyces cerevisiae* yeast cell or a *Yarrowia lipolytica* yeast cell.

Embodiment 63

An expression construct including an exogenous fungi transcription terminating nucleic acid sequence of any one of embodiments 1 to 54.

Embodiment 64

A method of expressing a gene in a fungi cell, the method including: (i) transforming the fungi cell with an expression construct including a gene operably linked to an exogenous fungi transcription terminating nucleic acid sequence of any one of embodiments 1 to 54; (ii) allowing the cell to express the expression construct, wherein the exogenous fungi transcription terminating nucleic acid sequence modulates a level of transcription of the gene, thereby expressing the gene in the fungi cell.

Embodiment 65

The method of embodiment 64, wherein the exogenous fungi transcription terminating nucleic acid sequence increases the level of transcription of the gene when compared to a control.

Embodiment 66

The method of embodiment 64, wherein the exogenous fungi transcription terminating nucleic acid sequence decreases the level of transcription of the gene when compared to a control.

Embodiment 67

The method of any one of embodiments 64 to 66, wherein the exogenous fungi transcription terminating nucleic acid sequence increases the half-life of a mRNA expressed from the gene when compared a control.

Embodiment 68

The method of any one of embodiments 64 to 66, wherein the exogenous fungi transcription terminating nucleic acid sequence decreases the half-life of a mRNA expressed from the gene when compared a control.

What is claimed is:

1. A fungal cell comprising an exogenous fungal transcription terminating nucleic acid sequence, wherein said fungal transcription terminating nucleic acid sequence comprises:
   (i) an efficiency nucleic acid sequence of the formula $(TA)_{n1}$, wherein n1 is an integer from 4 to 20;
   (ii) a positioning nucleic acid sequence of the formula AAWAAA, wherein W is A or T; and
   (iii) a polyadenylation site nucleic acid sequence comprising the sequence $(N)_{n4}$ $Y$-$A_{n2}$, wherein
   N is A, C, T, or G;
   n4 is an integer from 0 to 10;
   Y is a polyadenylation site nucleotide and is C or T; and
   n2 is an integer from 3 to 50.

2. The exogenous fungal transcription terminating nucleic acid sequence of claim 1, wherein n1 is 4-15.

3. The exogenous fungal transcription terminating nucleic acid sequence of claim 1, wherein n1 is 10-14.

4. The exogenous fungal transcription terminating nucleic acid sequence of claim 1 comprising the sequence:

$$X^1 \text{-} (TA)_{n1} \text{-} L^1 \text{-} AAWAAA \text{-} L^2 \text{-} ((N)_{n4} Y \text{-} A_{n2}),$$ (Sequence I)

wherein n1 is an integer from 10-20;

$X^1$ is absent or an upstream nucleic acid sequence 2 to 20 nucleotides in length;

AAW AAA is said positioning nucleic acid sequence;

$(N)_{n4}$ $Y$-$A_{n2}$ is said polyadenylation site nucleic acid sequence;

$L^1$ is a first linking nucleic acid sequence linking said positioning nucleic acid sequence to said efficiency nucleic acid sequence and $L^2$ is a second linking nucleic acid sequence linking said positioning nucleic acid sequence to said polyadenylation site nucleic acid sequence, wherein said first linking nucleic acid sequence and said second linking nucleic acid sequence are independently 5 to 30 nucleotides in length.

5. The exogenous fungal transcription terminating nucleic acid sequence of claim 4, wherein $X^1$ is an upstream nucleic acid sequence 6 to 12 nucleotides in length.

6. The exogenous fungal transcription terminating nucleic acid sequence of claim 4, wherein n1 is 12.

7. The exogenous fungal transcription terminating nucleic acid sequence of claim 4, wherein W is T.

8. The exogenous fungal transcription terminating nucleic acid sequence of claim 4, wherein n4 is an integer from 1 to 4 nucleotides and n2 is an integer from 3 to 10.

9. A fungal cell comprising an exogenous fungal transcription terminating nucleic acid sequence, wherein said fungal transcription terminating nucleic acid sequence comprises:
   (i) an efficiency nucleic acid sequence of the formula $(TA)_{n1}$, wherein n1 is an integer from 3 to 20;
   (ii) a positioning nucleic acid sequence of the formula AAWAAA, wherein W is A or T;
   (iii) a polyadenylation site nucleic acid sequence comprising the sequence $(N)_{n4}$ Y-$A_{n2}$, wherein
   N is A, C, T, or G;
   n4 is an integer from 0 to 1 O;
   Y is a polyadenylation site nucleotide and is C or T; and
   n2 is an integer from 3 to 50; and
   (iv) a first linking nucleic acid sequence linking said positioning nucleic acid sequence to said efficiency nucleic acid sequence or a second linking nucleic acid sequence linking said positioning nucleic acid sequence to said polyadenylation site nucleic acid sequence, wherein said first linking nucleic acid sequence and said second linking nucleic acid sequence are independently 3 to 30 nucleotides in length and consist of less than about 35% of cytosine and guanine.

10. The exogenous fungal transcription terminating nucleic acid sequence of claim 9, wherein said first linking nucleic acid sequence or said second linking nucleic acid sequence consists of less than about 30% cytosine and guanine.

11. The exogenous fungal transcription terminating nucleic acid sequence of claim 9, wherein said first linking nucleic acid sequence is about 10-25 nucleotides in length.

12. A fungal cell comprising an exogenous fungal transcription terminating nucleic acid sequence, wherein said fungal transcription terminating nucleic acid sequence comprises:
   (i) an efficiency nucleic acid sequence of the formula $(TA)_{n1}$, wherein n1 is an integer from 3 to 20;
   (ii) a positioning nucleic acid sequence of the formula AAWAAA, wherein W is A or T;
   (iii) a polyadenylation site nucleic acid sequence comprising the sequence $(N)_{n4}$ Y-$A_{n2}$, wherein
   N is A, C, T, or G;
   n4 is an integer from 0 to 10;
   Y is a polyadenylation site nucleotide and is C or T; and
   n2 is an integer from 3 to 50;
   (iv) an upstream nucleic acid sequence 5' to said efficiency nucleic acid sequence of the formula $(T)_{n3}$, wherein n3 is an integer from 2 to 20.

13. The exogenous fungal transcription terminating nucleic acid sequence of claim 12, wherein n1 is an integer of 3 to 12.

14. The exogenous fungal transcription terminating nucleic acid sequence of claim 12, wherein n3 is an integer from 4 to 12.

15. The exogenous fungal transcription terminating nucleic acid sequence of claim 12, further comprising a first linking nucleic acid sequence linking said positioning nucleic acid sequence to said efficiency nucleic acid sequence.

16. The exogenous fungal transcription terminating nucleic acid sequence of claim 1, wherein said exogenous fungal transcription terminating nucleic acid sequence includes a length of less than about 200 nucleotides.

17. An expression construct comprising an exogenous fungi transcription terminating nucleic acid sequence of claim 1.

18. A method of expressing a gene in a fungal cell, said method comprising:
   (i) transforming the fungal cell of claim 1 with an expression construct comprising a gene operably linked to the exogenous fungal transcription terminating nucleic acid sequence;
   (ii) allowing said cell to express said expression construct, wherein said exogenous fungal transcription terminating nucleic acid sequence modulates a level of transcription of said gene, thereby expressing said gene in said fungal cell.

* * * * *

UNITED STATES PATENT AND TRADEMARK OFFICE
CERTIFICATE OF CORRECTION

PATENT NO.         : 9,951,344 B2
APPLICATION NO.    : 14/879946
DATED              : April 24, 2018
INVENTOR(S)        : Hal Alper et al.

Page 1 of 1

It is certified that error appears in the above-identified patent and that said Letters Patent is hereby corrected as shown below:

In the Claims

In Claim 9, Line 12 "n4 is an integer from 0 to 1 O" should read "n4 is an integer from 0 to 10"

Signed and Sealed this
Twenty-sixth Day of June, 2018

Andrei Iancu
*Director of the United States Patent and Trademark Office*

SEQUENCE LISTING

```
<160> NUMBER OF SEQ ID NOS: 64

<210> SEQ ID NO 1
<211> LENGTH: 45
<212> TYPE: DNA
<213> ORGANISM: Artificial sequence
<220> FEATURE:
<223> OTHER INFORMATION: Synthetic polynucleotide

<400> SEQUENCE: 1
tatatatata taactgtcta gaaataaaga gtatcatctt tcaaa                45

<210> SEQ ID NO 2
<211> LENGTH: 57
<212> TYPE: DNA
```

```
<213> ORGANISM: Artificial sequence
<220> FEATURE:
<223> OTHER INFORMATION: Synthetic polynucleotide

<400> SEQUENCE: 2
tatatatata tatatatata tataactgtc tagaaataaa gagtatcatc tttcaaa         57

<210> SEQ ID NO 3
<211> LENGTH: 69
<212> TYPE: DNA
<213> ORGANISM: Artificial sequence
<220> FEATURE:
<223> OTHER INFORMATION: Synthetic polynucleotide

<400> SEQUENCE: 3
tatatatata tatatatata tatatatata tataactg tctagaaata aagagtatca        60
tctttcaaa                                                              69

<210> SEQ ID NO 4
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 4
actgtctaga aataaagagt atcatctttc aaa                                   33

<210> SEQ ID NO 5
<211> LENGTH: 37
<212> TYPE: DNA
<213> ORGANISM: Artificial sequence
<220> FEATURE:
<223> OTHER INFORMATION: Synthetic polynucleotide

<400> SEQUENCE: 5
tataactgtc tagaaataaa gagtatcatc tttcaaa                               37

<210> SEQ ID NO 6
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 6
tatatattta ataaagagta tcatctttca aa                                    32

<210> SEQ ID NO 7
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 7
tatataactg tctagaaata aatttttca aa                                     32

<210> SEQ ID NO 8
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 8
```

```
tatataaact catttactta tgtaggaata aagagtatca tctttcaaa       49
```

<210> SEQ ID NO 9
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 9

```
tatataactg tctagaaata aaaactcatt tacttatgta ggtttcaaa       49
```

<210> SEQ ID NO 10
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 10

```
tatatacacc cgtcgagcct gtccgaaata aagagtatca tctttcaaa       49
```

<210> SEQ ID NO 11
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 11

```
tatataactg tctagaaata aacacccgtc gagcctgtcc gatttcaaa       49
```

<210> SEQ ID NO 12
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 12

```
tatataggtg caggcaaata aagagtatca tctttcaaa                  39
```

<210> SEQ ID NO 13
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 13

```
tatataactg tctagaaata aaggtgcagg catttcaaa                  39
```

<210> SEQ ID NO 14
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 14

```
tatataactg tctagaaata aagagtatca tctaaaaa                   38
```

<210> SEQ ID NO 15
<211> LENGTH: 36
<212> TYPE: DNA

<213> ORGANISM: Artificial sequence
<220> FEATURE:
<223> OTHER INFORMATION: Synthetic polynucleotide

<400> SEQUENCE: 15
tatataactg tctagaaata aagagtatca tccaaa                                36

<210> SEQ ID NO 16
<211> LENGTH: 38
<212> TYPE: DNA
<213> ORGANISM: Artificial sequence
<220> FEATURE:
<223> OTHER INFORMATION: Synthetic polynucleotide

<400> SEQUENCE: 16
tatataactg tctagaaata aagagtatca tccaaaaa                              38

<210> SEQ ID NO 17
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 17
tatataactg tctagaaaaa aagagtatca tctttcaaa                             39

<210> SEQ ID NO 18
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 18
tatataactg tctagaaata aagagtatca tctttcaaat tttttttt                   49

<210> SEQ ID NO 19
<211> LENGTH: 47
<212> TYPE: DNA
<213> ORGANISM: Artificial sequence
<220> FEATURE:
<223> OTHER INFORMATION: Synthetic polynucleotide

<400> SEQUENCE: 19
ttttttttta taactgtc tagaaataaa gagtatcatc tttcaaa                      47

<210> SEQ ID NO 20
<211> LENGTH: 59
<212> TYPE: DNA
<213> ORGANISM: Artificial sequence
<220> FEATURE:
<223> OTHER INFORMATION: Synthetic polynucleotide

<400> SEQUENCE: 20
cgcattggcc ggccaatgcg tatataactg tctagaaata aagagtatca tctttcaaa       59

<210> SEQ ID NO 21
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 21
aatcaaattc tatataactg tctagaaata aagagtatca tctttcaaa                  49

<210> SEQ ID NO 22
<211> LENGTH: 48
<212> TYPE: DNA
<213> ORGANISM: Artificial sequence
<220> FEATURE:
<223> OTHER INFORMATION: Synthetic polynucleotide

<400> SEQUENCE: 22
tgggtggtat atataactgt ctagaaataa agagtatcat ctttcaaa        48

<210> SEQ ID NO 23
<211> LENGTH: 48
<212> TYPE: DNA
<213> ORGANISM: Artificial sequence
<220> FEATURE:
<223> OTHER INFORMATION: Synthetic polynucleotide

<400> SEQUENCE: 23
gtggtatgtt atataactgt ctagaaataa agagtatcat ctttcaaa        48

<210> SEQ ID NO 24
<211> LENGTH: 51
<212> TYPE: DNA
<213> ORGANISM: Artificial sequence
<220> FEATURE:
<223> OTHER INFORMATION: Synthetic polynucleotide

<400> SEQUENCE: 24
tgggtggtat gttatataac tgtctagaaa taaagagtat catctttcaa a      51

<210> SEQ ID NO 25
<211> LENGTH: 65
<212> TYPE: DNA
<213> ORGANISM: Artificial sequence
<220> FEATURE:
<223> OTHER INFORMATION: Synthetic polynucleotide

<400> SEQUENCE: 25 tttttttta tatatata tatatata taactgtcta gaaataaaga gtatcatctt    60
tcaaa                                                           65

<210> SEQ ID NO 26
<211> LENGTH: 67
<212> TYPE: DNA
<213> ORGANISM: Artificial sequence
<220> FEATURE:
<223> OTHER INFORMATION: Synthetic polynucleotide

<400> SEQUENCE: 26
aatcaaattc tatatatata tatatatata taactgtc tagaaataaa gagtatcatc  60
tttcaaa                                                          67

<210> SEQ ID NO 27
<211> LENGTH: 66
<212> TYPE: DNA
<213> ORGANISM: Artificial sequence
<220> FEATURE:
<223> OTHER INFORMATION: Synthetic polynucleotide

<400> SEQUENCE: 27
tgggtggtat atatatatat atatatatat ataactgtct agaaataaag agtatcatct  60
ttcaaa                                                             66

<210> SEQ ID NO 28
<211> LENGTH: 66
<212> TYPE: DNA
<213> ORGANISM: Artificial sequence
<220> FEATURE:
<223> OTHER INFORMATION: Synthetic polynucleotide

<400> SEQUENCE: 28
gtggtatgtt atatatatat atatatatat ataactgtct agaaataaag agtatcatct    60
ttcaaa    66

<210> SEQ ID NO 29
<211> LENGTH: 69
<212> TYPE: DNA
<213> ORGANISM: Artificial sequence
<220> FEATURE:
<223> OTHER INFORMATION: Synthetic polynucleotide

<400> SEQUENCE: 29
tgggtggtat gttatatata tatatatata tataactg tctagaaata aagagtatca    60
tctttcaaa    69

<210> SEQ ID NO 30
<211> LENGTH: 68
<212> TYPE: DNA
<213> ORGANISM: Artificial sequence
<220> FEATURE:
<223> OTHER INFORMATION: Synthetic polynucleotide

<400> SEQUENCE: 30 tttttttta tatatatata tatatata taaactcatt tacttatgta ggaataaatt    60
ttttcaaa    68

<210> SEQ ID NO 31
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 31
tatataactg tctagaaata aagagtatca tctttcaaa    39

<210> SEQ ID NO 32
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 32
tatataactt tttaaaaata aaaaaatttt ttttcaaa    39

<210> SEQ ID NO 33
<211> LENGTH: 8
<212> TYPE: DNA
<213> ORGANISM: Artificial sequence
<220> FEATURE:
<223> OTHER INFORMATION: Synthetic polynucleotide

<400> SEQUENCE: 33 tttttttt    8

<210> SEQ ID NO 34
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 34
cgcattggcc ggccaatgcg                                        20

<210> SEQ ID NO 35
<211> LENGTH: 10
<212> TYPE: DNA
<213> ORGANISM: Artificial sequence
<220> FEATURE:
<223> OTHER INFORMATION: Synthetic polynucleotide

<400> SEQUENCE: 35
aatcaaattc                                                   10

<210> SEQ ID NO 36
<211> LENGTH: 9
<212> TYPE: DNA
<213> ORGANISM: Artificial sequence
<220> FEATURE:
<223> OTHER INFORMATION: Synthetic polynucleotide

<400> SEQUENCE: 36 tgggtggta                                                     9

<210> SEQ ID NO 37
<211> LENGTH: 9
<212> TYPE: DNA
<213> ORGANISM: Artificial sequence
<220> FEATURE:
<223> OTHER INFORMATION: Synthetic polynucleotide

<400> SEQUENCE: 37 gtggtatgt                                                     9

<210> SEQ ID NO 38
<211> LENGTH: 12
<212> TYPE: DNA
<213> ORGANISM: Artificial sequence
<220> FEATURE:
<223> OTHER INFORMATION: Synthetic polynucleotide

<400> SEQUENCE: 38
tgggtggtat gt                                                12

<210> SEQ ID NO 39
<211> LENGTH: 10
<212> TYPE: DNA
<213> ORGANISM: Artificial sequence
<220> FEATURE:
<223> OTHER INFORMATION: Synthetic polynucleotide

<400> SEQUENCE: 39
actgtctaga                                                   10

<210> SEQ ID NO 40
<211> LENGTH: 20
<212> TYPE: DNA
<213> ORGANISM: Artificial sequence
<220> FEATURE:
<223> OTHER INFORMATION: Synthetic polynucleotide

```
<400> SEQUENCE: 40
aactcattta cttatgtagg                                            20

<210> SEQ ID NO 41
<211> LENGTH: 10
<212> TYPE: DNA
<213> ORGANISM: Artificial sequence
<220> FEATURE:
<223> OTHER INFORMATION: Synthetic polynucleotide

<400> SEQUENCE: 41
gagtatcatc                                                       10

<210> SEQ ID NO 42
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 42
cacccgtcga gcctgtccga                                            20

<210> SEQ ID NO 43
<211> LENGTH: 10
<212> TYPE: DNA
<213> ORGANISM: Artificial sequence
<220> FEATURE:
<223> OTHER INFORMATION: Synthetic polynucleotide

<400> SEQUENCE: 43
ggtgcaggca                                                       10

<210> SEQ ID NO 44
<211> LENGTH: 3
<212> TYPE: DNA
<213> ORGANISM: Artificial sequence
<220> FEATURE:
<223> OTHER INFORMATION: Synthetic polynucleotide

<400> SEQUENCE: 44 ttt                                                               3

<210> SEQ ID NO 45
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 45
tatatatttt ttttaaaata aaaaaaattt tctttcaaa                       39

<210> SEQ ID NO 46
<211> LENGTH: 7
<212> TYPE: DNA
<213> ORGANISM: Artificial sequence
<220> FEATURE:
<223> OTHER INFORMATION: Synthetic polynucleotide

<400> SEQUENCE: 46 tttcaaa                                                           7

<210> SEQ ID NO 47
<211> LENGTH: 34
```

```
<212> TYPE: DNA
<213> ORGANISM: Artificial sequence
<220> FEATURE:
<223> OTHER INFORMATION: Synthetic polynucleotide

<400> SEQUENCE: 47
tgactgagct catagcctca aaatgtttct actc                                    34

<210> SEQ ID NO 48
<211> LENGTH: 45
<212> TYPE: DNA
<213> ORGANISM: Artificial sequence
<220> FEATURE:
<223> OTHER INFORMATION: Synthetic polynucleotide

<400> SEQUENCE: 48
ggcgctacta gttctagaaa acttagatta gattgctatg ctttc                        45

<210> SEQ ID NO 49
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 49
caaagagctc ctagtacgga ttagaagccg                                         30

<210> SEQ ID NO 50
<211> LENGTH: 30
<212> TYPE: DNA
<213> ORGANISM: Artificial sequence
<220> FEATURE:
<223> OTHER INFORMATION: Synthetic polynucleotide

<400> SEQUENCE: 50
ggcgctacta gttctagaat ccggggtttt                                         30

<210> SEQ ID NO 51
<211> LENGTH: 41
<212> TYPE: DNA
<213> ORGANISM: Artificial sequence
<220> FEATURE:
<223> OTHER INFORMATION: Synthetic polynucleotide

<400> SEQUENCE: 51
ggcgctacta gtatgtctaa aggtgaagaa ttattcactg g                            41

<210> SEQ ID NO 52
<211> LENGTH: 37
<212> TYPE: DNA
<213> ORGANISM: Artificial sequence
<220> FEATURE:
<223> OTHER INFORMATION: Synthetic polynucleotide

<400> SEQUENCE: 52
acgcgtcgac ttatttgtac aattcatcca taccatg                                 37

<210> SEQ ID NO 53
<211> LENGTH: 26
<212> TYPE: DNA
<213> ORGANISM: Artificial sequence
<220> FEATURE:
<223> OTHER INFORMATION: Synthetic polynucleotide

<400> SEQUENCE: 53
```

```
catcggccga tggtgagcaa gggcga                                              26

<210> SEQ ID NO 54
<211> LENGTH: 32
<212> TYPE: DNA
<213> ORGANISM: Artificial sequence
<220> FEATURE:
<223> OTHER INFORMATION: Synthetic polynucleotide

<400> SEQUENCE: 54
ttagccggcc aaattaaagc cttcgagcgt cc                                       32

<210> SEQ ID NO 55
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 55
ttctgtctcc ggtgaaggtg aa                                                  22

<210> SEQ ID NO 56
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 56
taaggttggc catggaactg gcaa                                                24

<210> SEQ ID NO 57
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 57
tcaagaccac ctacaaggcc aaga                                                24

<210> SEQ ID NO 58
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 58
acagttccac gatggtgtag tcct                                                24

<210> SEQ ID NO 59
<211> LENGTH: 24
<212> TYPE: DNA
<213> ORGANISM: Artificial sequence
<220> FEATURE:
<223> OTHER INFORMATION: Synthetic polynucleotide

<400> SEQUENCE: 59
atcgtgaaat tgcaggcagc ttgg                                                24

<210> SEQ ID NO 60
<211> LENGTH: 24
<212> TYPE: DNA
<213> ORGANISM: Artificial sequence
```

```
<220> FEATURE:
<223> OTHER INFORMATION: Synthetic polynucleotide

<400> SEQUENCE: 60
catggcaacg gcagaaggca ataa                                          24

<210> SEQ ID NO 61
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 61
ccttaattaa gctgcttgta cctagtgcaa ccccagtttg ttaaaaatta gtagtcaaaa   60

<210> SEQ ID NO 62
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 62
gcgccgttta aacactgagt gacagagccc tctcatgttt ggagagaaga ctaagtacaa   60

<210> SEQ ID NO 63
<211> LENGTH: 60
<212> TYPE: DNA
<213> ORGANISM: Artificial sequence
<220> FEATURE:
<223> OTHER INFORMATION: Synthetic polynucleotide

<400> SEQUENCE: 63
ccttaattaa gcgtctacaa ctggacccct agcctgtata tatcaattga ttatttaaag   60

<210> SEQ ID NO 64
<211> LENGTH: 46
<212> TYPE: DNA
<213> ORGANISM: Artificial sequence
<220> FEATURE:
<223> OTHER INFORMATION: Synthetic polynucleotide

<400> SEQUENCE: 64
gcgccgttta aacgacgcaa gagaagccgt cgcccacgg agtatc                   46
```